United States Patent [19]

Herrlich et al.

[11] Patent Number: 5,506,119
[45] Date of Patent: Apr. 9, 1996

[54] DNA ENCODING VARIANT CD44 SURFACE PROTEINS ASSOCIATED WITH METASTATIC TUMORS

[75] Inventors: Peter Herrlich, Karlsruhe; Helmut Ponta, Linkenheim, both of Germany; Ursula Guenthert, Basel, Switzerland; Siegfried Matzku, Wiesenbach; Achim Wenzel, Heidelberg, both of Germany

[73] Assignees: Kernforschungszentrum Karlsruhe GmbH; Universitaet Karlsruhe, both of Karlsruhe; Deutsches Krebsforschungszentrum, Heidelberg, all of Germany

[21] Appl. No.: 946,497

[22] PCT Filed: Mar. 30, 1991

[86] PCT No.: PCT/EP91/00614

§ 371 Date: Nov. 9, 1992

§ 102(e) Date: Nov. 9, 1992

[87] PCT Pub. No.: WO91/17248

PCT Pub. Date: Nov. 14, 1991

[30] Foreign Application Priority Data

May 7, 1990 [DE] Germany ............... 40 14 510.7

[51] Int. Cl.⁶ .................. A61K 35/12; C07K 14/205; C12N 15/12
[52] U.S. Cl. ............ 435/69.3; 424/184.1; 424/185.1; 424/277.1; 530/350; 530/300; 530/395; 530/828; 435/172.3; 435/252.3; 435/320.1; 536/23.1; 536/23.5
[58] Field of Search ............... 424/88, 184.1, 424/185.1, 277.1; 435/69.3, 172.3, 320.1, 252.3; 536/23.5, 23.1; 935/9, 10, 12; 530/300, 350, 395, 828

[56] References Cited

PUBLICATIONS

Lehmann, J. M. et al. Proc. Natl. Acad. Sci USA 86: 9891–9895 (1989).
Chan, B. M. C. et al. Science 251: 1600–1602 (1991).
Maniatis T. et al. Molecular Cloning pp. 382–389 Cold Spring Harbor Laboratory (1982).
Kugelman, L. C. et al. J. Invest. Dermotol. 99:381–385 (1992).
Bowvie, J. V. et al. Science 247: 1306–1310 (1990).
Kumar, V. et al. Proc. Natl. Acad. Sci. 87: 1337–1341 (1990).
Ellis, R. W. In: Vaccines, Protkin & Mortiner Eds. W. B. Saunders Co. (1988) pp. 568–575.
Young, R. A. et al. Proc. Natl. Acad. Sci. 80: 1194–1198 (1983).
Birnbaum et al., "Amplification, Expression and Localization of the c–myc Gene in BSp73 Rat Tumor Cell Lines," Anticancer Research, vol. 8, 1988, pp. 1185–1191.
Matzku et al., "Antigenic Differences between Metastatic and Nonmetastatic BSp73 Rat Tumor Variants Characterized by Monoclonal Antibodies," Cancer Research, vol. 49, Mar. 1, 1989, pp. 1294–1299.

*Primary Examiner*—Christine M. Nucker
*Assistant Examiner*—Michael Tuscan
*Attorney, Agent, or Firm*—Foley & Lardner

[57] ABSTRACT

The presence of certain extracellular regions ("ECR") from human and rat variants of the CD44 membrane glycoprotein have been found to be associated with metastasis ability in tumor cells. Isolated polynucleotides encoding the ECRs permit expression of the ECR polypeptide, which in turn can be used as an antigen to obtain monoclonal antibodies that recognize the ECR polypeptide. The anti-ECR monoclonal antibodies have the ability to prevent metastasis by tumor cells that would otherwise metastasize and spread.

5 Claims, 12 Drawing Sheets

```
   1                                                                 CTCATTGCCCCAGCAGCCCCCAGTCACACGTTCCATTCACCCTCTTTGCCCC

113 ATGGACAAGGTTTGTGGCACACAGCTTGGGGACTACTTTGCCCTCTTACACTTGAGCCTGCCA
     M  D  K  V  C  G  T  Q  L  G  D  Y  F  A  L  L  H  L  S  L  .  A

233 AAAAATGGGCGCTACAGTATCTCCAGGACTGAAGCAGCTGACCTCTGCAGGCTTTCAACACC
     K  N  G  R  Y  S  I  S  R  T  E  A  A  D  L  C  E  A  F  N  T

353 AGGTATGGGTTCATAGAAGGACACGTTGTAATCCCCAGGATCCACCCCAACCCTATCTGCA
     R  Y  G  F  I  E  G  H  V  V  I  P  R  I  H  F  H  A  I  C  A

473 TATTGCTTCAATGCCTCAGCTCCTCTTGAAGAAGACTGTACATCGTCAGACCTACCCAAT
     Y  C  F  N  A  S  A  P  L  E  E  D  C  T  S  V  T  D  L  P  N

593 AAGAAGGGCGAGTATAGAACACACAAGAAGACATCCATCCCTCAAACATTATAGATCAGGAT
     K  K  G  E  Y  R  T  H  Q  E  D  I  D  A  S  N  I  D  E  D

713 GACCTTCCCACTTCCACAGCCTCACTGGAGACCGGGGATCACGCCCTTCTTATTGGAGCACCCTC
     D  L  P  T  S  Q  P  T  G  D  R  D  D  A  F  F  I  G  S  T  L

833 ACCCAGTGGAACCCGATCCATTCAAACCCAGAAGTACTACTTCAGACAACCACCAGGATGACT
     T  Q  W  N  P  I  H  S  N  P  E  V  L  L  Q  T  T  T  R  M  T

953 CCTCCTTTCAATAACCATGAGTATCAGGATGAAGAGGAGACCCCACATGCTACAAGCACAACC
     P  P  F  N  N  H  E  Y  Q  D  E  E  E  T  P  H  A  T  S  T  T

1073 GAGAATGAATGGCAGGGGAAGAACCCACCCACCCAAGTGAACACTCCCATGTGACACAGAAGG
     E  N  E  W  Q  G  K  N  P  P  T  P  S  E  D  S  H  V  T  E  G

1193 CAGGATGTTTCATGGACCCATTCTTCGACCCAATCTCCATCCAATGGGACAAGGTCATCAA
     E  D  V  S  W  T  D  F  F  D  P  P  I  S  H  P  M  G  Q  G  H  Q
```

```
TTCCCCCGCCACCCTTTTCCAGAGGCTACTAGATCCTTGGTTTCATCCTGCACATC

CAGGACCAGATCCATTTGAATATAACCTCCCGTTACCCACGTGTATTCCATCTCCAC
 Q  Q  Q  I  D  L  N  I  T  C  R  Y  A  G  V  F  H  V  E

ACCTTCCCCACCATGGCTCAGATGGAGTTACCCCTGAGAAAGGGTTTCAAACATCC
 T  L  P  T  M  A  Q  M  E  L  A  L  R  K  G  F  E  T  C

CCCAACAACACAGGAGTGTATATCCTCCTCGCCATCCAACACCTCCACTATCACACA
 A  N  N  T  G  V  Y  I  L  L  A  S  N  T  S  H  Y  D  T

TCCTTCCATGGACCAGTTACCATAACTATTGTCAACCGTCATGGCACCCGCTACAGC
 S  F  D  G  P  V  T  I  T  I  V  N  R  D  G  T  R  Y  S

GTCAGGAGTCGATCCACCATTGAGAAGAGCACCCCCAGAAGGCTACATTTTCCACACC
 V  S  S  G  S  T  I  E  K  S  T  P  E  G  Y  I  L  H  T

CCCACCATTGCAACTACTCCATGGGTTTCTGCCCACACAAAACAGAACCAGGAACGG
 A  T  I  A  T  T  F  W  V  S  A  H  T  K  Q  N  Q  E  R

GATATAGACAGAAACAGCACCAGTGCTCATGGAGAAACTGGACCCAGGAACCACAG
 D  I  D  R  N  S  T  S  A  H  G  E  N  W  T  Q  E  P  Q

TGGGCAGATCCTAATAGCAACAAGAAGCAGCTACCCAGAAGGACAAGTGGTTT
 W  A  D  P  N  S  T  T  E  E  A  A  T  Q  K  E  K  W  F

ACAACTCCCTCAGCCCTACAACAACCATCCAAGTCAAAGAATGACACAGAGTCAA
 T  T  A  S  A  H  N  N  H  P  S  Q  R  M  T  T  Q  S  Q

ACAGAAAGCAAGGACACTCAAGTGGAATCAAGACAGTGGAGTCACCACAACTTCT
 T  E  S  K  G  H  S  S  G  N  Q  D  S  G  V  T  T  T  S
```

```
1313  GGTCCTCGCGAGGAGACCTCAGATTCCACACTGCCTTATCATCTTCCCATCCCTCCTCCCCTG
       G  P  A  R  R  P  Q  I  P  E  W  L  T  I  L  A  S  L  L  A  L

1433  AAGAAGCTGGTGATCAACAGTGGCAATGGAACAGTGGAAGACAGGAACCAAGTCAACTCAAC
       K  K  L  V  I  N  S  G  N  G  T  V  E  D  R  K  P  S  E  L  N

1553  ACTCCCGACCAGTTTATCACACTGCCATCGACACCCGAATCTGCCAGACTGTGGATATCAAGATT
       T  P  D  Q  F  M  T  A  D  E  T  R  N  L  Q  S  V  D  M  K  I

1673  TACTGGGAGCTGGGACCCTTAACACAGATGCAATGTGCTACTGATTATTTTTATTGGCATTATT

1793  AATAGCATTGCTTTCTGAAATGAGGGTCTCTTCCAGTTCCTCCTTAGAGGCCTTGCATTACCA

1913  AGTCCCAGGTAACATCCACCACCTAAGGATTTCCCCAGAACTTAGACAGATTGGTCTCTGGGA

2033  GCAGTGGATGGGAGATCAGGTGTACTGGTTACACACTCTCTTTATACACTCCCTTCTGCTGA

2153  GCTATTTATCTTTGTTTTTGAAATATCAAACATCTGTCCATCTTCCATCTTGACCTGTTGTCTGCTGATCCTT

2273  ATAAGTTGATTCATAATAAATACCTGTCCATCTTGACCTGTTGTCTGCTGATCCTT

2393  GGTCCTCTGAAACTCATGTTAGAGCATCCGTGCCCTGCCCTGGGTTACCCAGCTGAATCTCAG

2513  TGTTCAAGAATCTGAATTGGCAGTAGGAGAGCTTCGTCGTCCCTTTATCGTTTCGATAACCACCC

2633  GTTTCATAGACACTGATCTTATTGGCACTTTCACAAAACAGTGTGGAGGGACTTCTGACACC

2753  GCATGAGGAGGCATGATGTACAACCCCAGACCACTCTTTCCATCACCACATTGTTGATGCT

2873  AAGAATGCCCACCCCTGGAATCTTACCACCACCAGATCACCACCTTATCGTTTAGCAAAAGG

2993  CCAGGATGCCCCATTGCTCCTCCAGGTCTTCCCAGGTACCTTGTACAAGAACTTAAATCTATAAA

3113  TAAATTTATATGTTAATAGTTTTTTTCAAATAAAAACAAACACAAAAAGGAAAAAAAAAA
```

```
CCTCTCATTCTTCCCCTCTGCATTCCTCTCAACAGTAGGAGAAGCTGTCGGCACAAC
 A  L  I  L  A  V  C  L  A  V  N  S  P  P  C  C  Q  E
GGCCACCCCAGCAAGTCTCAGGAAATCGTGCCATTTGGTCAACAACCAACACAC
 G  E  A  S  E  S  Q  E  M  V  H  L  V  N  E  E  P  T  E
GGGCTGTAGTCCCTATGCCACTAACTTGAAAAGACACAACAATTCGACACATCTCAT
 G  V  H
TTGGGCATAAAATTTCCCTTTTTTTGTTTTTAAAAGTTTGTTTTCCAATTTATCAA
GGGTATGCTACCATAGGCTTCTACCAAATGAATACTCTTGGTCCCGATTGAACCCAA
CGAAATTTCAATGGCTCCCAGCAGTCCAATCTCTAGGCATTGCTTT
AAATTTCCACATGCTTCTGAGAGATTCCCCAAAGTGACGCTATTTATCTTTACTAA
TATTTTTGTTTTTATTTGTTTTTTAGGTTACTTTGTCTCACAACCATAACACGGT
CACTTTCTAAATCACCAAGCTCTCACTCTTTGTACCACATCAATCTCACCTTACTAT
AAGATCAAGCAGGAGCACTGTTTCATTCTAGGACTATCAAAGGGCTTTCTCTCC
ATTTCTCTTTCTTAAACGCCACATTAACTTTTTATATCTTACAACATTCCCCCTCCT
TTATAGTAAAAGGAGAAGCCAACAGAAATGAAAGTGTGGACAGAGAGCAGTAGATTG
TTCGCAAGCCAGTTGGTACTTAGAATCAGTTCCCAGGAATCCTTCAAAAAGCCAT
ACAATCCTCTCACCCTCGACCTCATACTTTCACATACTCCCCAAGTCTTCATCTG
ATAACCCTTTCTCTAAAATCGAACTTCCTTCTAAGGCTCCCATTTTTACTGTTGAC
AAAAAAAAAAAAAAAAAAAAAAAAAAAAAAAAAA
```

FIG. 3a(1)

```
 716  GTACACCCCATCCCAGACGAAGACAGTCCCTGCA
 201   V  H  P  I  P  D  E  D  S  P  W
 205   S  Q  P  T  G  D  R  D  D  A  F

821  GACAGACACCTCAGTTTTTCTGGATCAGGCATTG
 236   D  R  H  L  S  F  S  G  S  G  I
 245   D  K  Y  P  N  F  S  G  S  G  I

941  TGGAACCCAAGCCATTCAAATCCGGAAGTGCTAC
 276   W  N  P  S  H  S  N  P  E  V  L
 285   W  N  P  I  H  S  N  P  E  V  L

1061  CTCATTCACCATGAGCATCATGAGGAAGAAGAGA
 316   L  I  H  H  E  H  H  E  E  E  E
 325   F  N  N  H  E  Y  Q  D  E  E  E

1181  AGATGGCATGAGGGATATCGCCAAACACCCAGAG
 358   R  W  H  E  G  Y  R  Q  T  P  R
 365   E  W  Q  G  K  N  P  P  T  P  S

1301  GACAGTTCCTGGACTGATTTCTTCAACCCAATCT
 396   D  S  S  H  T  D  F  F  N  P  I
 404   D  V  S  H  T  D  F  F  D  P  I

1421  CCAAACACAGGTTTCGTGGAAGATTTGGACAGGA
 436   P  N  T  G  L  V  E  D  L  D  R
 443   P  N  T  H  L  V  E  D  L  N  R

1541  CCAACAACTTCTACTCTGACATCAAGCAATAGGA
 476   P  T  T  S  T  L  T  S  S  N  R
 483   P  T  T  S  V  L  P  S  S  T  K

1661  ACGAAGGAAAGCAGGACCTTCATCCCAGTGACCT
 516   T  K  E  S  R  T  F  I  P  V  T
 520   T  M  E  N  G  T  L  F  P  V  T
```

FIG. 3a(2)

```
TCACCGAC---------------AGCACAGACAGAATC
 I  T  D  -  -  -  -  -  S  T  D  R  I
 F  I  G  S  T  L  A  T  S  T  E  S  N
                              ┌─► D II

ATGATGATGAAGATTTTATCTCCAGCACCATTTCAACC
 D  D  D  E  D  F  I  S  S  T  I  S  T
 D  D  D  E  D  F  I  S  S  T  I  A  T

TTCAGACAACCACAAGGATGACTGATGTAGACAGAAAT
 L  Q  T  T  T  R  M  T  D  V  D  R  N
 L  Q  T  T  T  R  M  T  D  I  D  R  N
                    ┌─► D III

CCCCACATTCTACAAGCACAATCCAGGCAACTCCTAGT
 T  P  H  S  T  S  T  I  Q  A  T  P  S
 T  P  H  A  T  S  T  T  H  A  D  P  N

AAGACTCCCATTCGACAACAGGGACAGCTGCAGCCTCA
 E  D  S  H  S  T  T  G  T  A  A  A  S
 E  D  S  H  V  T  E  G  T  -  T  A  S

CACACCCCATGGGACGAGGTCATCAAGCAGGAAGAAGG
 S  H  P  H  G  R  G  H  Q  A  G  R  R
 S  H  P  M  G  Q  G  H  Q  T  E  S  K

CAGGACCTCTTTCAATGACAACGCAGCAGAGTAATTCT
 T  G  P  L  S  M  T  T  Q  Q  S  N  S
 T  G  P  L  S  V  T  T  P  Q  S  N  S
           ┌─► D V

ATGATGTCACAGGTGGAAGAAGAGACCCAAATCATTCT
 N  D  V  T  G  G  R  R  D  P  N  H  S
 -  -  -  S  G  R  R  R  G  G  S  L  P

CAGCTAAGACTGGGTCCTTTGGAGTTACTGCAGTTACT
 S  A  K  T  G  S  F  G  V  T  A  V  T
 P  A  K  T  E  V  F  G  E  T  E  G  T
```

FIG. 3a(3)

```
         D I
CCTGCTACCACAGGCTGGGAGCCAAATGAAGAAAATGAAGATGAAAGA
  P  A  T  T  G  H  E  P  N  E  E  N  E  D  E  R      human
  T  N  P  T  G  H  K  P  N  E  E  N  E  D  E  T      rat ACACCACGGGCCTTTGACCACACAAAACAGAACCAGGACTGGACCCAG
  T  P  R  A  F  D  H  T  K  Q  N  Q  D  W  T  Q      human
  T  P  W  V  S  A  H  T  K  Q  N  Q  E  R  T  Q      rat GGCACCACTGCTTATGAAGGAAACTGGAACCCAGAAGCACACCCTCCC
  G  T  T  A  Y  E  G  N  W  N  P  E  A  H  P  P      human
  S  T  S  A  N  G  E  N  W  T  Q  E  P  Q  P  P      rat AGTACAACGGAAGAAACAGCTACCCAGAAGGAACAGTGGTTTGGCAAC
  S  T  T  E  E  T  A  T  Q  K  E  Q  W  F  G  N      human
  S  T  T  E  E  A  A  T  Q  K  E  K  W  F  E  N      rat GCTCATACCAGCCATCCAATGCAAGGAAGGACAACACCAAGCCCAGAG
  A  N  T  S  N  P  M  Q  G  R  T  T  P  S  P  E      human
  A  N  N  N  N  P  S  Q  R  M  T  T  Q  S  Q  E      rat
         D IV
ATGGATATGGACTCCAGTCATAGTACAACGCTTCAGCCTACTGCAAAT
  M  D  M  D  S  S  H  S  T  T  L  Q  P  T  A  N      human
  -  D  T  G  S  S  H  S  T  T  L  Q  P  T  A  A      rat CAGAGCTTCTCTACATCACATGAAGGCTTGGAAGAAGATAAAGACCAT
  Q  S  F  S  T  S  H  E  G  L  E  E  D  K  D  H      human
  Q  N  F  S  T  L  P  G  E  L  E  E  G  E  D  H      rat GAAGGCTCAACTACTTTACTGGAAGGTTATACCTCTCATTACCCACAC
  E  G  S  T  T  L  L  E  G  Y  T  S  H  Y  P  H      human
  R  D  T  T  T  S  L  E  G  Y  T  P  Q  Y  P  D      rat
         end of variant domaine GTTGGA---GATTCCAACTCTAATGTCAATCGTTCCTTATCAGGAGAC
  V  G  -  D  S  N  S  N  V  N  R  S  L  S  G  D      human
  V  A  T  D  S  N  F  N  V  D  G  S  L  P  G  D      rat
```

```
rMeta-1  QEPQPFNNHEYQDEETPHATSTTWADPNSTTEEAATQK         316
hCD44    ------------------------------------          -
mCD44    ------------------------------------          - rMeta-1  EKWFENEWQGKNPPTPSEDSHVTEGTTASAHNHPSQRMT        356
hCD44    -------------------------------------         -
mCD44    -------------------------------------         - rMeta-1  TQSQEDVSWTDFFDPISHPMGQGHQTESK-------           385
hCD44    SSRTTHGSELAGHSSANQDSGVTTPMRRPQIPEWLI           232
mCD44    GFDTTVGSELADGHSHGSGSQEGANTPHRTPIPEWLI          233
rCD44    GSHTTVGSELAHSSGHSSPGVTTSGPARRPIPEWLI           234 rMeta-1  ILASLLALILAVCIAVNSRRRCGQKKLVINSGNGTVE          453
hCD44    ILASLLALILAVCIAVNSRRRCGQKKLVINSGNGAVE          312
mCD44    ILASLLALILAVCIAVNSRRRCGQKKLVINGGNGTVE          313 rMeta-1  DRKPSELNGEASKSQEMVHLVNKEPTETPDQFMTADETRN       493
hCD44    DRKPSGLNGEASKSQEMVHLVNKESSETPDQFMTADETRN       352
mCD44    DRKPSELNGEASKSQEMVHLVNKEPSETPDQCMTADETRN       353 rMeta-1  LQSVDMKIGV                                    503
hCD44    LQNVDMKIGV                                    362
mCD44    LQSVDMKIGV                                    363
```

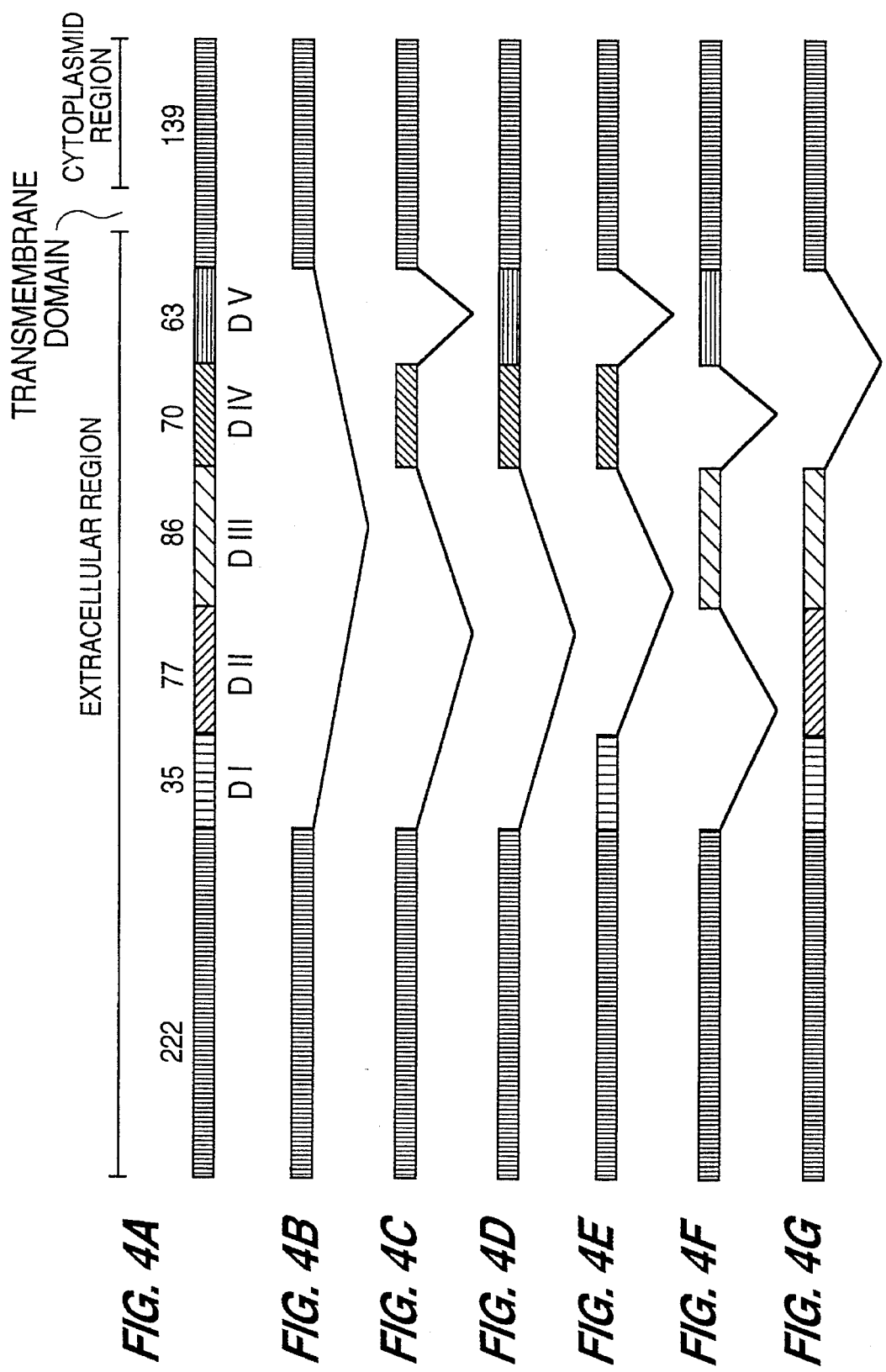

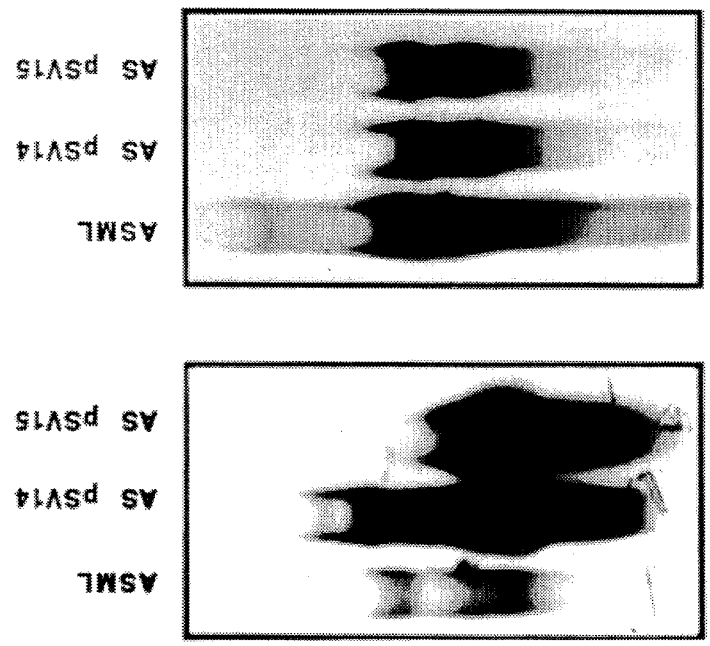
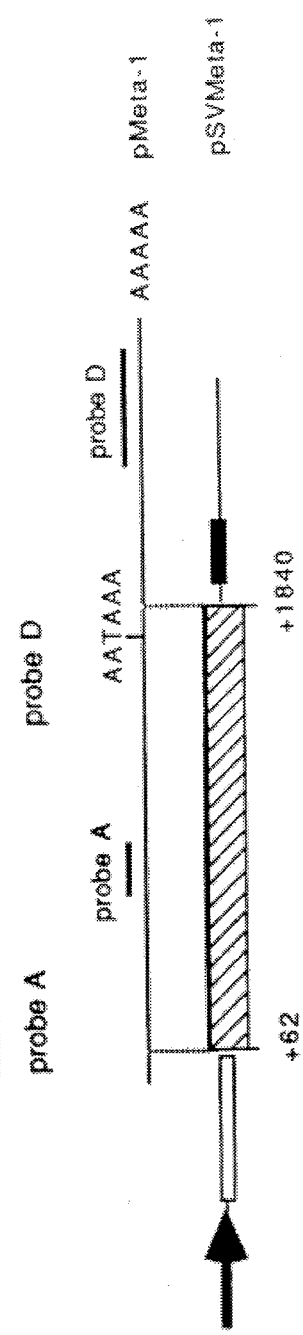
FIG. 5

DNA ENCODING VARIANT CD44 SURFACE PROTEINS ASSOCIATED WITH METASTATIC TUMORS

The invention concerns variant CD44 surface proteins, antibodies against the variant determinants of these proteins, as well as processes for their production, furthermore the DNA sequences which code for these variant protein fragments, as well as the use of these proteins or parts thereof and the antibodies directed against them for the diagnosis and therapy of tumour metestases.

BACKGROUND OF THE INVENTION

The ability to metastase forms the actual life-endangering property of malignant tumour cells. The original primary tumour cells probably acquire this property by a whole series of changes in the course of the tumour progression. As a result of this process, cancer cell variants are continuously detached from the primary tumour mass, penetrate the extracellular matrix and migrate into the lymphatic system or the blood circulation. Often adhering to one another, the metastasing tumour cells are transported in the blood or lymph system, leave the vascular system at other places in order there to penetrate into secondary tissue and form daughter tumours (survey of Hart et al., 1989; Nicolson, 1987). The formation of metastases requires a whole series of interactions of the tumour cells with intercellular matrix and other cells. Almost all of these interactions require cell surface components, such as e.g. the receptors for matrix and lamina, surfacebound proteolytic enzymes, as well as cell adhesion molecules with inclusion of those which cause organspecific adhesion and thus organ preference of the metastasis, furthermore growth factors and growth factor receptors.

It is known that the membrane proteins differentiate non-metastasing and metastasing tumour cells of the BSp73 rat tumours, demonstrated by antibody reaction (Matzku et al., 1983 and 1989).

SUMMARY OF THE INVENTION

It has now been found that the metastasing BSp73ASML tumour cells contain a surface protein which, in part, corresponds to a known glycoprotein participating in the lymphocyte adhesion and cell-cell and cell-matrix exchange action (designation of the normal glycoprotein in humans: CD44, hermes-1, in the mouse: Ppg-1 and in the rat: HEBFln). However, the new variant CD44 surface protein differs from these known sequences by an extracellular region (ECR) of 154 amino acids which is introduced between the 220th and 237th amino acid of the human CD44 sequence (or 224th and 239th amino acid of the mouse sequence). This new glycoprotein appears to possess an important role for the cell/matrix or cell/cell binding in the case of the metastasis. Therefore, the production and characterisation of this protein region (ECR) forms one of the tasks of the present invention. By immunisation of mice with membrane proteins which have been obtained from BSp73ASML, spleen cells were produced which form antibodies against the ECR of the variant CD44 surface protein. According to the method of Köhler (1981), these are fused by polyethylene glycol with myeloma cells in order to produce permanent cultures. By means of cloning and selection of those cultures which produce antibodies which react with BSp73ASML but not with the non-metastasing parent form and also not with other non-tumorigenic rat cells, there can be obtained specific antibodies against the new protein part ECR. For the further investigation, a monoclonal antibody was chosen which stains the BSp73ASML cells in the immunofluorescence test especially intensively, which has received the designation mAb1.1ASML (mAb: monoclonal antibody).

In the Western blot test, in a protein hydrolysate frown BSp73ASML, there can be determined 4 protein bands with molecular weights of 120,000; 150,000; 180,000 and 200,000 with mAb1.1.ASML, whereas extracts from rat fibroblast cells and non-metastasing rat tumour cells give no significant reaction. It has not yet been possible to determine whether these size differences are due to a different original amino acid sequence or to a differently strong subsequent protein modification. In any case, the epitope recognised by the antibody is contained in all 4 protein species but not in the proteins serving for the control from the non-metastasing BSp73As cells or from normal rat cells.

Isolation of cDNA sequences which code for the ECR of the surface protein

The monoclonal antibody mAb1.1ASML was used in order to discover the ECR-coding cDNA sequences in a bacterial expression bank. The bank was constructed with the help of PolyA+ RNA from BSp73ASML and the pEX vector system (Stanley & Luzio, 1984). The products coded by the cDNA sequences are found as β-galactosidase fusion proteins with the help of the antibodies. A so-isolated cDNA clone positive for the monoclonal antibody 1.1ASML with the name pEX34 carries a cDNA sequence piece of 167 nucleotides. This cDNA piece was now used in order to pattern through a larger cDNA bank in the vector pSP65, again from BSp73ASML RNA. One of these clones isolated therewith, pM66, served thereto to isolate the total length cDNA clone pMeta-1 with the help of so-called "primer" elongation (starter oligonucleotides) and of the polymerase chain reaction (PCR). Evidence of the total length was obtained with the help of the primary elongation (3207 nucleotides). The colinearity with an RNA from the BSp73ASML tumour was documented by RNase and S1 protection analysis.

BRIEF DESCRIPTION OF THE FIGURES

FIGS. 2a–2d depict the sequence of the CD44 protein and DNA from p-Meta-1. The signal peptide is represented by "......". The ECR is represented by "–". The transmembrane region is represented by "\\\\\".

FIGS. 3a(1)–3a(3) depict the nucleotide and protein sequence of a human extracellular region and compares the protein sequence to a rat sequence, and FIGS. 3b(1)–3b(2) compare protein sequences of rat rMeta-1, human hCD44 and mouse mCD44.

FIGS. 4A–4G depict patterns of RNA derived from CD44.

FIG. 5 depicts RNA patterns from G418-resistant and p-Meta-1 expressing BSp73AS cells.

Figure 1:
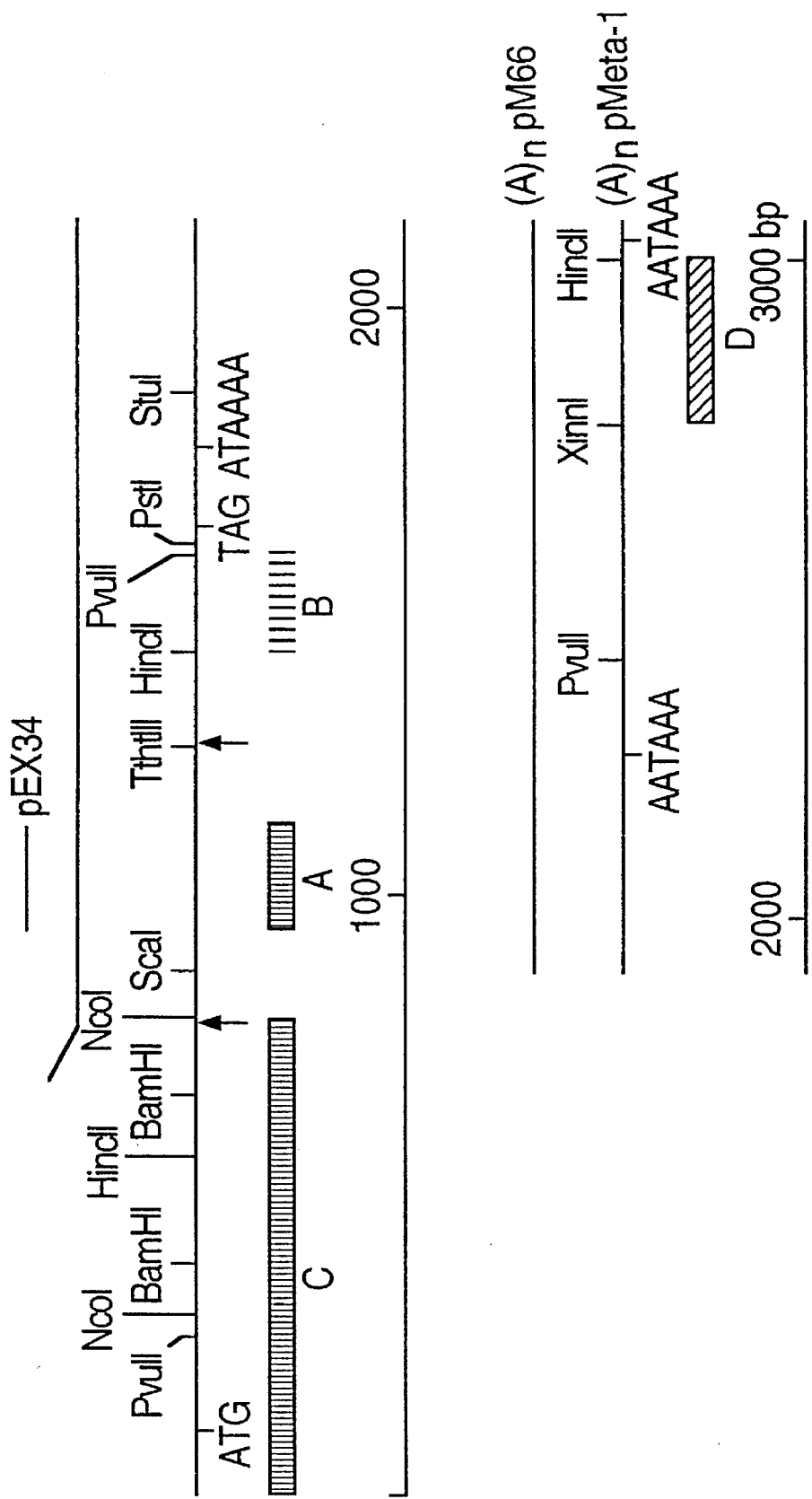
FIG. 1 depicts the structure of a cDNA of the rat surface protein p-Meta-1. Bar "A" represents the extracellular region ("ECR") at positions 941–1108. Bar "B" represents the sequence between positions 1403–1572. Bar "C" represents the sequence between the starting position to position 794. Bar "D" represents sequences at the end of the cDNA clone.

The isolation of the cDNAs with the help of the expression in bacteria and the recognition by the antibodies proved that the antibody recognised primary amino acid sequence in the ECR of the surface protein.

ECR-coding messenger RNA is expressed in BSp73ASML but not in BSp73AS cells.

Three different sequence samples were produced from the cDNA clones in order to demonstrate specific messenger RNAs by hybridisation. A sample A covers the cDNA region which codes for the ECR (positions: 941– 1108). The sample B represents sequences between the positions 1403–157.2 and sample C carries sequences. from the start up to position 794 from pMeta-L (FIG. 1). Poly A+ RNA of the BSp73 tumour cell line was separated electrophoretically and analysed with the help of RNA transfer hybridisation. Four of the cell lines, which do not metastase, contain no RNA which is homologous to the sample A, whereas RNAs from the metastasing tumour cells strongly react BSp73ASML. In this RNA preparation, the sample A recognises a heterogenous mixture of various RNA sizes between 2.2 and 3.3 kb and a larger RNA species of 4.9 kb. The exclusive expression of the specific membrane proteins recognised by the monoclonal antibody 1.1ASML in the metastasing tumour cell variant is obviously based upon the exclusive expression of the corresponding ECR-coding messenger RNAs. Obviously the complete cDNA clone pMeta-1 with 3.2 kb cannot represent all sequences of this RNA species. It can only represent one species from the heterogenous mixture of RNA sizes. The samples B and C give the same hybridisation pattern as sample A in the separation of the BSp73ASML RNA in any case as far as one can ascertain in the heterogeneity, i.e. these RNA species carry sequences which are complementary to all three samples, A, B and C. In contradistinction to sample A, sample B and C also recognise messenger RNA species in the non-metastasing cell lines. However, the RNA sizes differ clearly from those in BSp73ASML, there are, namely, detected four clearly differentiatable messenger RNA species with the sizes 1.5, 2.0, 2.9 and 4.3 kb. Although these RNA species could be hidden in the heterogenous mixture of the RNAs from BSp73ASML, it is, nevertheless, certain that they do not exist in the same amount in the BSp73ASML. It is decisive that RNA sequences with complementarity to sample A are obviously completely absent in the non-metastasing cells. Therefore, we can carefully conclude that the sequences of the samples A, B and C are contained in the same RNAs in the metastasing tumour, namely, in a manner as though sample A sequences have been spliced into the B-C-positive RNAs and as though this alternative splicing process only occurred in the metastasing cell line.

In order to demonstrate the colinearity between RNA and cDNA and in order to analyse the difference of the RNAs between the BSp73AS and the BSp73ASML cells, S1 nuclease and RNase protection analyses were carried out. The protected DNA or RNA fragments could only be smaller than the total length because they contain 5'-end vector sequences which cannot hybridise with the RNAs from the tumour cells. We consider first the transfer to the 3' side: the transfer of sequences with homology to sample A to those to sample B. Both techniques show a single RNA species in BSp73AS which is colinear with the samples over a wide range. Furthermore, 5' thereof differentiate cDNA or RNA sample, which certainly correspond to RNA sequences from BSp73ASML, from the RNA from the BSp73AS cells. In particular, the RNAs from BSp73ASML contain sequences which protect larger fragments of the samples. The largest fragments correspond to the full length of the DNA or RNA pieces which were offered for the protection analysis. Smaller fragments are also detectable. Since the RNA transfer hybridisations have certainly uncovered a heterogenous mixture of different sizes of RNAs, it is possible that these indicate smaller protected fragments of RNA species which diverge elsewhere from the cDNA, i.e. at positions between the previously detected divergence point and the 5' end of the offered samples. The RNA species are also not detectable in the BSp73AS cells.

We now consider the point of the divergence on the 5' side, thus the transition of sequences which hybridise with the sample C to those which hybridise with the sample A, thus the ECR-coding sequence. The analysis gives corresponding results for the 5' breaking point. RNAs from BSp73AS can protect the offered samples only over a small range. Messenger RNAs from BSp73ASML protect longer fragments. They are, namely, colinear over the whole length of the offered sample. One can thus conclude that the cDNA clone represents pMeta-1 sequences which are distinctive in the metastasing tumour cells BSp73ASML. The 3' and 5' regions are also found in RNAs from BSp73AS. The ECR-coding sequences with the definite transitions, which can be mapped with the help of these above-described techniques, indicate that here an alternative splicing mechanism must be present for the RNA formation. The 5' and 3' breakage points of the transitions to the ECR sequences are marked by arrows in FIG. 1.

The monoclonal antibody 1.1ASML identifies a variant form of the glycoprotein CD44.

In order to obtain structural information about the surface protein, all cloned cDNA molecules have been sequenced. The nucleotide sequence of the total length clone pMeta-1 and the amino acid sequences derived therefrom are shown in FIGS. 2a–2d (SEQ ID NOS 1 and 2). The total length cDNA clone traverses 3207 nucleotides (SEQ ID NO:1). The 3' terminus carries a PolyA end, two additional polyadenylation signals lie at positions 2288 and 1743. The first ATG codon follows a consensus initiation sequence and opens a readiag frame of 1509 nucleotides, corresponding to 503 amino acids (SEQ ID NO:2). As one should assume for a membranestanding protein, the first 21 amino acids are hydrophobic and represent a signal peptide. No part of these sequences is hitherto to be found in the data bases. However, we found sequence homology to the recently published data about the lymphocyte homing receptor CD44 (of Pgp-1) (Idzerda et el., 1989; Goldstein et al., 1989; Stamenkovic et al., 1989; Nottenburg et al., 1989; Zhou et al., 1989). The homologies are strictly limited to the 5' and 3' parts of the cDNA with inclusion of non-translated regions and they end at the already above-mentioned points of divergence between the BSp73AS and the BSp73ASML RNA sequences. The total extent between the divergence points (in FIG. 2 characterised by colour markings), thus the whole extent of the metastasis-specific ECR-coding sequence, is not represented in the Pgp1 or CD44 sequences. The metastasis-specific glycoprotein obviously represents a variant of the CD44 glycoproteins. It carries, namely, an additional extracellular domain of 156 amino acids and thus an expanded extracellular region of 410 amino acids (less 21 amino acid signal peptide), in comparison with 270 amino acids (also less signal peptide) of the unchanged CD44 glycoprotein. However, in the non-metastasing BSp73AS cells, the unchanged forms of this CD44 family are detected. cDNA sequences of these BSp73AS RNAs have also been cloned and the identity with the metastasis-specific clones outside Of the extra domain is demonstrated.

The expression of the variant CD44 is correlated with the metastatic potential.

In order to test whether the expression of the variant CD44 glycoproteins takes place without exception in the BSp73ASML cells and whether it stands in connection with the metastatic potential of these cells or with the metastatic potential in general, we studied a series of isogenic rat tumour cell lines, namely, the tumour cell lines of the mammary carcinoma system 13762 NF (Neri et al., 1982). We here compare cell lines which have been derived from the parental tumour, namely, the MTPa, MTC, MTF7 and MTA cells (group 1), with cell lines which were established from lymph nodes or lung metastases, namely, MTLy, MTLn2, MTLn3 (group 2). The group 1 cells essentially express the normal CD44 pattern similarly to the RNAs from the BSp73AS cells when one hybridises with sample B. On the other hand, with sample A, there is detected a smaller amount of a diffuse RNA band which has about the size 2.5 kb. On the other hand, the group 2 cells show a completely different RNA pattern. Both samples A and B hybridise with larger RNA species. The sizes resemble those which are detected with BSp73ASML. The similarity is also documented by RNAse and S1 protection analyses. On the basis of these data, we conclude that a change of the splicing pattern of the RNA and the expression of variant CD44 is correlated with the formation of metastases and that the acquired pattern in these metastasing mammary carcinoma cells corresponds very much to those which we have already got to know for the metastasing BSp73ASML cell line. The high molecular proteins recognised by the antibodies correspond to the two high molecular species of proteins which were detected in the BSp73ASML extracts. In this mammary tumour series, we thus discovered also a metastasis-specific expression of RNA species and of high molecular proteins. That in the group 1, thus the so-called parenteral cell lines, any RNAs were found at all which hybridised with the sample A, thus the ECR-coding sequence, and that we can also see a weak coloration of a protein of 100,000 Dalton with the antibody, we attribute to the fact that the group 1 cells also possess small metastasing ability quite contrary to our original cell line BSp73AS which shows no metastasing behaviour at all.

The monoclonal antibody 1.1ASML inhibits matastasis formation in the rat.

In a series of experiments for the metastasis formation of the tumour cell line BSp73ASML in isogenic rats, cells were injected subcutaneously and at different times the monoclonal antibody 1.1ASML was injected intraperitoneally at intervals of two to three days before and after the tumour administration. In the scope of this immunological protocol, it was also determined how the immune response of the rat towards the injected antibody had taken place. There result, namely, anti-mouse immunoglobulin antibodies, as well as also anti-idiotype antibodies. The result of this series of experiments is that the growth and the metastasing of the tumour is considerably delayed by injection of 1.1ASML. This delay permits, in its kinetic, the conclusion that the antibody interferes with a primary process of the metastasing. The experiment shows to us that the protein structure on the surface of the metastasing cells recognised by the antibody has a role in the metastasing process and that therapeutic and diagnostic plans are realistic.

Isolation of the homologous human sequence for the ECR-coding sequence part of the rat cDNA.

For human tumour cells in culture, the possibility naturally does not exist as a matter of course of detecting, correspondingly the rat system, whether they also still retain metastasing properties. Experiments with immune-deficient mice make possible only very limited predictions regarding the metastasis potential in the case of humans. Therefore, relatively many tumour cell lines, which have been taken up in culture anywhere in the world at points of time lying a long time ago, would have to be tested for whether they express the sequences which we could detect for the rat metastases. It has been possible to find such a tumour cell line. It originates from a large-cell lung carcinoma of humans and bears the number: LCLC97. In this tumour cell line can be detected three definite. RNA species (sizes: 5.5; 3.4 and 2.8 kb) which behave quite corresponding to the RNAs which are detectable in the metastasing tumour cell lines of the rat. They hybridise, namely, not only with the sample A but also with the samples B and C, i.e. that also these human RNA species are identical over wide ranges to the cDNA pMeta-1 (85%).

Figure 3B:
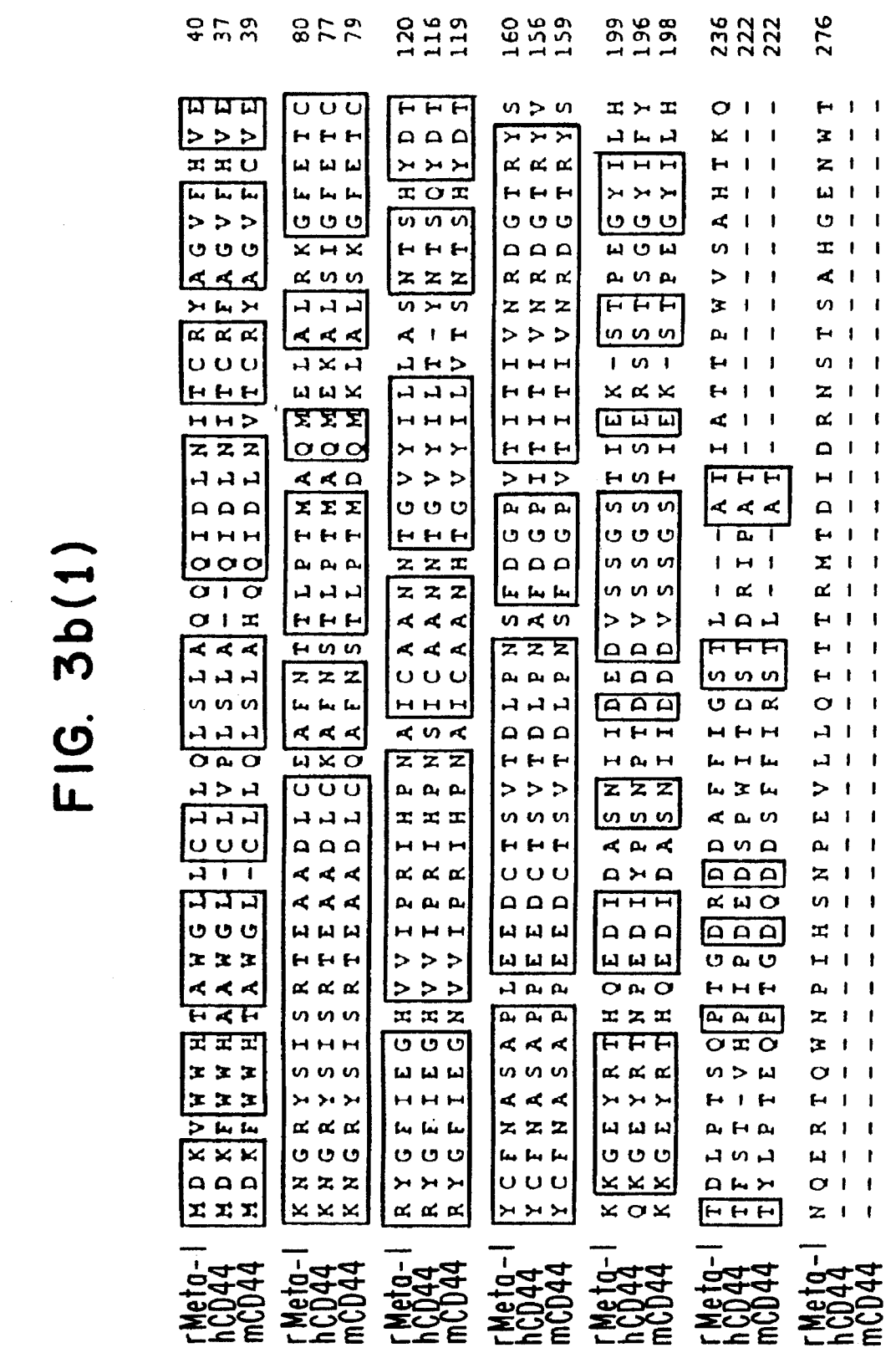

However, the monoclonal antibody 1.1ASML does not react with this tumour cell, i.e. the piece of protein recognised by the antibody must, in the region of the antigen determinant, differ from the proteins which exist on the surface of the human tumour cells. For the non-reactivity, there suffice already the smallest variations on the basis of the high specificity of the antibody. The human tumour cell LCLC97 now served the purpose of constructing a cDNA bank. On the basis of the high agreement between the rat and human sequences, a cDNA clone could be isolated which showed homology with the sample A. The human cDNA was sequenced. In FIGS. 3a(1)–3b(2) is shown the primary sequence and the amino acid sequence derived (SEQ ID NOS 3 and 4) therefrom. One can see that, over large regions, identicity exists between the rat (SEQ ID NO:5) and the human sequence. This human sequence (SEQ ID NO:3), as well as also the amino acid sequence (SEQ ID NO:4) derived therefrom, is also the subject of this Patent Specification. FIGS. 3b(1)–3b(2) also show the protein sequences of surface proteins for rat (rMeta-1, SEQ ID NO:2) human (hCD44, SEQ ID NO:6) and mouse (mCD44, SEQ ID NO:7) with extracellular regions in rat and human protein. rCD44 (SEQ ID NO:8) is also shown in this Figure.

Embodimental examples

Cells and antibodies

The following cloned Bsp cell lines were used for the investigation: BSp73 14ASML-1 and 10AS-7 and kept in culture as described by Matzku et al., (1983); furthermore, the mammary carcinoma cell lines described by Neri et al., (1982), monoclonal antibodies against BSp73 ASML membrane proteins were produced by immunisation of Balb c mice. After isolation of the spleen cells of an immunised mouse, these were fused with Ag8 myeloma cells for the immortalisation according to the method for the production of monoclonal antibodies of Köhler (1981). The then-obtained hybridoma cells were subjected to a screening process in order to find those which produce specific antibodies against BSp73ASML but not against BSp73AS and normal rat fibroblast cells. The precise procedure is described in the same way as by Matzku et al. (1989).

Monoclonal antibody (mAb)-producing hybridoma cells with the corresponding specificity were expanded in the tissue culture and the mAb given off into the medium highly enriched by ammonium sulphate precipitation and column chromatography (protein A-Sepharose and MonoQ) and used in this form for the investigations. One of them is mAb1.1ASML.

Immunofluorescence:

For the display of the variant CD44 molecule on different tumour cells, these were taken up in culture, then washed with phosphate-buffered common salt solution (PBS) and incubated with 1.1ASML for 30 minutes at 40° C. As secondary antibody for the detection of the binding, there was used a rhodamine-coupled rabbit anti-mouse IgG and shown in the fluorescence microscope.

Construction of the cDNA expression banks and immunoscreening.

PolyA+ RNA from BSp73ASML cells was "primed" with oligo (dT) and hexanucleotides of different composition and synthesised with reverse transcriptase from AMV of the first strand of the cDNA. The second strand of the cDNA was produced with *E. coli* DNA polymerase I, RNaseH and *E. coli* ligase and subsequently the doublestranded cDNA linearised on the ends with T4DNA. The vectors pEX1, 2 and 3 (Stanley and Luzio, 1984), which make possible the fusioning of the cDNA in 3 different reading rasters, were cleaved with SmaI restruction endonuclease and ligated with the cDNA (T4 DNA ligase). Competent *E. coli* DH5 (pCI857) bacteria, which produce a temperature-sensitive repressor, are transfected with the pEX-cDNA constructants and cultured on nylon filters. The gene for the temperature-sensitive repressor RCI857 lies on the plasmid pCI857, which is compatible with the pEX plasmids. At 28° C., the $1P_R$ promotor, which controls the synthesis of the fusion proteins, is inactivated. By temperature increase to 42° C., the CI repressor is inactivated and the synthesis of β-galactosidase/ASML fusion proteins massively set into action. The heat-induced bacteria colonies are subsequently denatured with chloroform vapour on the filters and these then incubated in PBS which contains 3% dry milk powder, lysozyme and DNase. The bacterial fusion proteins fixed on the nylon filter are now incubated with mAb1.1ASML and, after washing out of non-specifically-bound mAb, used for the detection of the binding as secondary antibody 125J-labelled rabbit anti-mouse IgG. After autoradiography, positive clones were isolated from the original bacteria filter and substantially analysed. One clone, which synthesised a fusion protein which reacted specifically with 1.1ASML, was pEX34. The pEX contained in the bacterial clone carries 167 nucleotide cDNA which, inter alia, codes for the epitope (or the antigen determinants), the specificity of which is carried by mAb1.1ASML.

The isolation of the total length cDNA mMeta-1 then took place according to standard methods.

Immunisation of the rats with mAb1.1ASML

BDX rats, which are syngenic to the BSp73 tumour cells, were injected subcutaneously or intraperitoneally with mAb1.1ASML (coupled to keyhole limpet haemocyananine), together with complete Freund's adjuvant. The first took place 10, 7 and 3 days before the injection of the BSpASML cells (into the fatty foot pad), the following then 3, 7, 11, 14 and 21 days thereafter. After 28 days, the rats were sacrificed, the various lymph nodes prepared and weighed and macroscopically visible lung metastases counted.

Connection between the expression of variant CD44 surface proteins and metastatic potential In order to ascertain whether the expression of variant CD44 glucoproteins is merely a property of the investigated BSp73ASML cell line or whether the expression can be brought into connection with the metasiatic potential, another series of rat tumour cells, which are derived from the 13762NF mammary carcinoma (Neri et al., 1982), were investigated. Furthermore, cell lines which were derived from the primary tumours (MTPa, MTC, MTF7 and MTA (group 1)) were compared with cell lines which are derived from lymph nodes and lung metastases (MTLy, MTLn2, MTLn3 (group 2)). The pattern of the RNA derived from CD44 is given in FIGS. 4A–4G, whereby samples A, B and D correspond to the samples described on pages 5 and 6 of the Application, as well as to FIG. 1. Cells of group 1 all show a normal CD44 pattern with sample B. However, cells of group 2 show a pattern different therefrom. The RNA is larger than the RNA of group 1 and corresponds to the RNA of BSp73ASML. Smaller RNAs are lost in the case of the hybridisation with sample D. The other patterns show the similarity between the two rat tumour systems.

Also with the sample A, the RNA pattern of group 2 corresponds to that of BSp73ASML. Whereas sample A does not hybridise with RNA from BSp73AS, there is shown a small diffuse RNA band of about 2.5 kb in the case of cells of group 1. RNase and S1 protection analysis also show the structural similarity. From these results, an exchange in the cleavage pattern and the expression of variant CD44 RNAs appears to take place with the formation of metastases.

Transfer of the metastatic potential to non-metastasing BSp73AS cells by overexpression of pMeta-1.

The connection of the expression of variant CD44 species with the metastatic potential in two series of rat tumours indicates a causal role of the glycoproteins in the metastatic process. In order to investigate this, pMeta-1 was transferred into BSp73AS cells and investigated whether the behaviour of the cells is thereby changed. The complete coding region of the pMeta-1 (FIGS. 2a–2d, SEQ ID NO:1) was inserted below the SV40 promotor and this formation (diagram in FIG. 5) introduced into the BSp73AS cells, together with PSV2neo. Individual G418-resistant and pMeta-1expressing colonies were obtained. The RNA pattern of 2 of these colonies is shown in FIG. 5. The hybridisation of the variant CD44-specific sample A shows a dominant transcript of approximately 2.2 kb which corresponds to the size of the smallest frequent RNA which is transcribed in BSp73ASML cells (FIG. 5). However, the transfected cells contain about 10 times as much of this RNA as BSp73ASML.

Other size orders are observed in one of the transfected cells (BSp73AS-pSVMeta-1-14), which could be dependent upon the place of the plasmid integration. A pSV2neo simulation transfer clone (not shown) and the BSp73AS receiver cells contain no RNA which is complementary to sample A. In order to discover the endogenic normal CD44 transcriptions (without the extra domains of the pSVMeta-1) in the transfects, the filter was stripped and rehybridised with sample D. This part of the non-transferred 3' sequence is not contained in the expression clone (cf. FIG. 5). Sample D detects two main transcripts of 2.9 and 4.9 kb in the RNA of the two transfects (FIG. 5, right column), not only in the control BSp73AS but also in the non-illustrated BSp73ASpSVneo.

Approximate quantifications of the various agreeing hybridisations show that the transfects express approximately 5× as much of the variant CD44 RNAs, which are transcribed by the expression plasmid, as the endogenic gene transcripts.

The overexpressed cDNA is transferred into a protein. The two transfects, which are illustrated in FIG. 5, synthesise mAbl-immune-colourable proteins of the same apparent size, namely, a main product of 150 kDa and a weaker band at 100 kDa. Since the cDNA sequence codes a primary protein product of only 503 amino acids (corresponds to about 60,000 Dalton), all visible bands must represent modified forms. The 150 kDa band runs together with one of the modified forms of variant CD44 which is expressed in the metastasing cells BSp73ASML. BSp73AS or simulation-transferred BSp73ASpSVneo do not possess this protein. As in BSp73ASML cells, the epitope of the cells expressed by the transfects lies freely on the cell surface.

In order to demonstrate that the expression of variant CD44 suffices in order to impart a metastatic potential to BSp73AS cells, transfects were injected into syngenic BDX rats (spontaneous metastasis protocol). In earlier experiments, metastatic tumour cells BSp73ASML spread out quickly from the place of the injection and were completely distributed about 10 days after the injection (Matzku, 1984). All local tumours were, therefore, removed by amputations on the 10th day. All carriers of BSp73ASML cells and all animals which had been injected with an overexpressing transfect developed lung metastases (Table 1). The course of the metastasis formation was comparably quick within 5–8 weeks after the injection. Animals which had received Bsp73AS cells or simulation transfects were, after this time, completely healthy (apart from due to the amputation) and even after 5 months no metastases could be ascertained.

In spite of a surprising similarity in the strong metastasis formation, there are some interesting differences. In all animals, BSp73ASML cells reach the lymph nodes and lead to a massive enlargement of various nodes in the region of the inguinal groin and next to the aorta (Table 1). A transfect (BSp73AS-pSV meta-1-14) causes lymph node enlargement in 3 of 8 animals although all animals develop lung metastases (Table 1). No lymph node enlargement is ascertainable with the other transfect (BSp73AS-pSV Meta-1-15). The transfects appear, therefore, to be able to form colonies in the lungs without an obligatory growth phase of the lymph nodes.

The experiment according to Table 1 further points to another difference between BSp73AS transfects and BSp73ASML. The individual lung metastases are macroscopically visible, whereas those of BSp73ASML are small and numerous but, in a larger series with BSp73ASML (Reber et al., 1990), 11 of 20 animals develop 5–20 larger nodes per lung than the transfects.

In order to ascertain that the metastases formed were brought about by the injected transfects and in order to exclude the improbable possibility of a spontaneous mutation, which transfers a metastatic potential, the epitope-positive proteins in the total lung extracts and in the extracts of recultured metastasis-producing cells were determined. The 150 kDa glycoprotein is detectable in the whole lung extract as well as in the extracts of a specific lung node from an animal which has received BSpAS-pSV meta-1-15 transfects. In the case of in vitro growth, the G418-resistant strain expresses a protein of the same apparent molecular weight.

Diagnosis and therapy

1. Analysis of human tumour material by in situ hybridisation with the human pMeta-1 sequence present. These experiments are considered as preliminary experiments before an Ab is available which recognises the human ECR.

2. Production of antibodies against the human ECR. Cloning of the human pMeta-1 sequences in bacterial expression vectors so that fusions arise with β-galactosidase or tryptophane E-product. Immunisation of rabbits with these fusion proteins or with synthesised peptides from the ECR (coupled to carrier molecules). Isolation of the polyvalent or monospecific antibodies.

Possibilities of use:

Immunohistological investigations of clinical tumour material (diagnosis)

Detection of soluble ECR in the serum of patients with the help of ELISA tests (diagnosis)

Construction of toxin-coupled antibodies in order, with the help of the antibody, to bring the toxin into the tumour/metastasis region (therapy)

Construction of antibodies with two definite antigen binding positions. By means of this double specificity, the attempt is to be made to initiate cytotoxic reactions in the metastasis region (e.g. anti CD2 or CD3 coupling) (therapy).

3. Production of hMeta-1 protein by transfection of human or rat cells with an expression vector which carries the complete hMeta-1 cDNA sequence; or purification from LCLC97 cells.

Possibilities of use:

Injection of the protein or parts thereof in order to block the tissue binding positions of the tumour cells After characterisation of the binding positions, a use for therapy would also be conceivable which could depend upon the injection of large amounts of binding protein which would then block the migrating tumour cells.

List of literature:

Goldstein, L. A., Zhou, D. F., Picker, L. J., Minty, C. N., Bargatz, R. F., Ding, J. F. and Butcher, E. C. (1989), A human lymphocyte homing receptor, the hermes antigen, is related to cartilage proteoglycan core and link proteins, Cell 56: 1063–1072.

Hart, I. R., Goode, N. T. and Wilson, R. E. (1989), Molecular aspects of the metastatic cascade, Biochim. Biophys. Acta 989: 65–84.

Idzerda, R. L., Carter, W. G., Nottenburg, C., Wayner, E. A., Gallatin, W. M. and St. John, T. (1989), Isolation and DNA sequence of a cDNA clone encoding a lymphocyte adhesion receptor for high endothelium, Proc. Natl. Acad. Sci. U.S.A. 86: 4659–4663.

Köhler, G. (1981) In: I. Lefkovits and B. Pernis (eds), Immunological Methods, Vol. 2, p.285, N.Y. Academic Press.

Matzku, S., Komitowski, Mildenberger and Zöller, M. (1983), Caharacterization of Bsp 73, a spontaneous rat tumor and its in vivo selected variants showing different metastasizing capacities, Inv. Met. 3: 109–123.

Matzku, S., Wenzel, A., Liu, S. and Zöller, M. (1989), Antigenic differences between metastatic and non-metastatic BSp73 rat tumor variants characterized by monoclonal antibodies, Cancer Res. 49: 1294–1299.

Neri, A., Welch, D., Kawaguchi, T. and Nicolson, G. L. (1982), Development and biologic properties of malignant cell sublines and clones of spontaneously metastasizing rat mammary adenocarcinoma, J. Natl. Cancer Inst. 68:507–517.

Nicolson, G. L. (1987), Tumor cell instability, diversification, and progression to the metastatic phenotype; from oncogene to oncofetal expression, Cancer Res. 47: 1473–1487.

Nottenburg, C., Rees, G. and St. John, T. (1989), Isolation of mouse CD44 cDNA: structural features are distinct from the primate cDNA, Proc. Natl. Acad. Sci. U.S.A. 86: 8521–8525.

Stamenkovic, I., Amiot, M., Pesando, J. M. and Seed, B. (1989), A lymphocyte molecule implicated in lymph node homing is a member of the cartilage link protein family, Cell 56: 1057–1062.

Stanley K. K. and Luzio, J. P. (1984), Construction of a new family of high efficiency bacterial expression vectors: identification of cDNA clones coding for human liver proteins, EMBO J. 3: 1429–1434.

Wenzel, A. (1986), Charakterisierung von Differenzierungsantigenen auf dem Rattentumor Bsp 73 mit Hilfe monoklonaler Antikörper (Characterisation of differentiation antigens on the rat tumour Bsp 73 with the help of monoclonal antibodies), Diploma Dissertation, University of Karlsruhe.

Zhou, D. F. H., Ding, J. F., Picker, L. F., Bargatze, R. F., Butcher, E. C. and Goeddel, D. V. (1989), Molecular cloning and expression of Pgp-1 - The mouse homolog of the human H-CAM (Hermes) lymphocyte homing receptor, J. Immunol. 143: 3390–3395.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 3207 base pairs
        ( B ) TYPE: nucleic acid
        ( C ) STRANDEDNESS: double
        ( D ) TOPOLOGY: linear ( v i i ) IMMEDIATE SOURCE:
        ( B ) CLONE: p-Meta-1

( i x ) FEATURE:
        ( A ) NAME/KEY: CDS
        ( B ) LOCATION: 113..1624

( x i ) SEQUENCE DESCRIPTION: SEQ ID NO:1:

```
CTCATTGCCC  AGCAGCCCCC  AGCCAGTGAC  AGGTTCCATT  CACCCTCTTT  GCCCCTTCCC      60

CCGCGACCCT  TTTCCAGAGG  CTACTAGATC  CTTTGGTTTC  ATCCTGCACA  TC ATG         115
                                                              Met
                                                               1

GAC  AAG  GTT  TGG  TGG  CAC  ACA  GCT  TGG  GGA  CTA  CTT  TGC  CTC  TTA  CAG    163
Asp  Lys  Val  Trp  Trp  His  Thr  Ala  Trp  Gly  Leu  Leu  Cys  Leu  Leu  Gln
               5                        10                       15

TTG  AGC  CTG  GCA  CAG  CAG  CAG  ATC  GAT  TTG  AAT  ATA  ACC  TGC  CGT  TAC    211
Leu  Ser  Leu  Ala  Gln  Gln  Gln  Ile  Asp  Leu  Asn  Ile  Thr  Cys  Arg  Tyr
               20                       25                       30

GCA  GGT  GTA  TTC  CAT  GTG  GAG  AAA  AAT  GGC  CGC  TAC  AGT  ATC  TCC  AGG    259
Ala  Gly  Val  Phe  His  Val  Glu  Lys  Asn  Gly  Arg  Tyr  Ser  Ile  Ser  Arg
          35                       40                       45

ACT  GAA  GCA  GCT  GAC  CTC  TGC  GAG  GCT  TTC  AAC  ACC  ACC  TTG  CCC  ACC    307
Thr  Glu  Ala  Ala  Asp  Leu  Cys  Glu  Ala  Phe  Asn  Thr  Thr  Leu  Pro  Thr
50                       55                       60                       65

ATG  GCT  CAG  ATG  GAG  TTA  GCC  CTG  AGA  AAG  GGG  TTT  GAA  ACA  TGC  AGG    355
Met  Ala  Gln  Met  Glu  Leu  Ala  Leu  Arg  Lys  Gly  Phe  Glu  Thr  Cys  Arg
                    70                       75                       80

TAT  GGG  TTC  ATA  GAA  GGA  CAC  GTG  GTA  ATC  CCG  AGG  ATC  CAC  CCC  AAC    403
Tyr  Gly  Phe  Ile  Glu  Gly  His  Val  Val  Ile  Pro  Arg  Ile  His  Pro  Asn
                85                       90                       95

GCT  ATC  TGT  GCA  GCC  AAC  AAC  ACA  GGA  GTG  TAT  ATC  CTC  CTC  GCA  TCC    451
Ala  Ile  Cys  Ala  Ala  Asn  Asn  Thr  Gly  Val  Tyr  Ile  Leu  Leu  Ala  Ser
          100                      105                      110

AAC  ACC  TCC  CAC  TAT  GAC  ACA  TAT  TGC  TTC  AAT  GCC  TCA  GCT  CCT  CTT    499
Asn  Thr  Ser  His  Tyr  Asp  Thr  Tyr  Cys  Phe  Asn  Ala  Ser  Ala  Pro  Leu
     115                      120                      125

GAA  GAA  GAC  TGT  ACA  TCA  GTC  ACA  GAC  CTA  CCC  AAT  TCC  TTC  GAT  GGA    547
Glu  Glu  Asp  Cys  Thr  Ser  Val  Thr  Asp  Leu  Pro  Asn  Ser  Phe  Asp  Gly
130                      135                      140                      145

CCA  GTT  ACC  ATA  ACT  ATT  GTC  AAC  CGT  GAT  GGC  ACC  CGC  TAC  AGC  AAG    595
Pro  Val  Thr  Ile  Thr  Ile  Val  Asn  Arg  Asp  Gly  Thr  Arg  Tyr  Ser  Lys
                    150                      155                      160

AAG  GGC  GAG  TAT  AGA  ACA  CAC  CAA  GAA  GAC  ATC  GAT  GCC  TCA  AAC  ATT    643
Lys  Gly  Glu  Tyr  Arg  Thr  His  Gln  Glu  Asp  Ile  Asp  Ala  Ser  Asn  Ile
                165                      170                      175

ATA  GAT  GAG  GAT  GTC  AGC  AGT  GGA  TCC  ACC  ATT  GAG  AAG  AGC  ACC  CCA    691
Ile  Asp  Glu  Asp  Val  Ser  Ser  Gly  Ser  Thr  Ile  Glu  Lys  Ser  Thr  Pro
          180                      185                      190

GAA  GGC  TAC  ATT  TTG  CAC  ACC  GAC  CTT  CCC  ACT  TCA  CAG  CCT  ACT  GGA    739
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Glu | Gly | Tyr | Ile | Leu | His | Thr | Asp | Leu | Pro | Thr | Ser | Gln | Pro | Thr | Gly |      |
|     | 195 |     |     |     |     | 200 |     |     |     |     | 205 |     |     |     |     |      |
| GAC | CGG | GAT | GAC | GCC | TTC | TTT | ATT | GGG | AGC | ACC | CTG | GCC | ACC | ATT | GCA | 787  |
| Asp | Arg | Asp | Asp | Ala | Phe | Phe | Ile | Gly | Ser | Thr | Leu | Ala | Thr | Ile | Ala |      |
| 210 |     |     |     |     | 215 |     |     |     |     | 220 |     |     |     |     | 225 |      |
| ACT | ACT | CCA | TGG | GTT | TCT | GCC | CAC | ACA | AAA | CAG | AAC | CAG | GAA | CGG | ACC | 835  |
| Thr | Thr | Pro | Trp | Val | Ser | Ala | His | Thr | Lys | Gln | Asn | Gln | Glu | Arg | Thr |      |
|     |     |     |     | 230 |     |     |     |     | 235 |     |     |     |     | 240 |     |      |
| CAG | TGG | AAC | CCG | ATC | CAT | TCA | AAC | CCA | GAA | GTA | CTA | CTT | CAG | ACA | ACC | 883  |
| Gln | Trp | Asn | Pro | Ile | His | Ser | Asn | Pro | Glu | Val | Leu | Leu | Gln | Thr | Thr |      |
|     |     |     | 245 |     |     |     |     | 250 |     |     |     |     | 255 |     |     |      |
| ACC | AGG | ATG | ACT | GAT | ATA | GAC | AGA | AAC | AGC | ACC | AGT | GCT | CAT | GGA | GAA | 931  |
| Thr | Arg | Met | Thr | Asp | Ile | Asp | Arg | Asn | Ser | Thr | Ser | Ala | His | Gly | Glu |      |
|     |     | 260 |     |     |     |     | 265 |     |     |     |     | 270 |     |     |     |      |
| AAC | TGG | ACC | CAG | GAA | CCA | CAG | CCT | CCT | TTC | AAT | AAC | CAT | GAG | TAT | CAG | 979  |
| Asn | Trp | Thr | Gln | Glu | Pro | Gln | Pro | Pro | Phe | Asn | Asn | His | Glu | Tyr | Gln |      |
|     | 275 |     |     |     |     | 280 |     |     |     |     | 285 |     |     |     |     |      |
| GAT | GAA | GAG | GAG | ACC | CCA | CAT | GCT | ACA | AGC | ACA | ACC | TGG | GCA | GAT | CCT | 1027 |
| Asp | Glu | Glu | Glu | Thr | Pro | His | Ala | Thr | Ser | Thr | Thr | Trp | Ala | Asp | Pro |      |
| 290 |     |     |     |     | 295 |     |     |     |     | 300 |     |     |     |     | 305 |      |
| AAT | AGC | ACA | ACA | GAA | GAA | GCA | GCT | ACC | CAG | AAG | GAG | AAG | TGG | TTT | GAG | 1075 |
| Asn | Ser | Thr | Thr | Glu | Glu | Ala | Ala | Thr | Gln | Lys | Glu | Lys | Trp | Phe | Glu |      |
|     |     |     |     | 310 |     |     |     |     | 315 |     |     |     |     | 320 |     |      |
| AAT | GAA | TGG | CAG | GGG | AAG | AAC | CCA | CCC | ACC | CCA | AGT | GAA | GAC | TCC | CAT | 1123 |
| Asn | Glu | Trp | Gln | Gly | Lys | Asn | Pro | Pro | Thr | Pro | Ser | Glu | Asp | Ser | His |      |
|     |     |     | 325 |     |     |     |     | 330 |     |     |     |     | 335 |     |     |      |
| GTG | ACA | GAA | GGG | ACA | ACT | GCC | TCA | GCC | CAC | AAC | AAC | CAT | CCA | AGT | CAA | 1171 |
| Val | Thr | Glu | Gly | Thr | Thr | Ala | Ser | Ala | His | Asn | Asn | His | Pro | Ser | Gln |      |
|     |     | 340 |     |     |     |     | 345 |     |     |     |     | 350 |     |     |     |      |
| AGA | ATG | ACA | ACA | CAG | AGT | CAA | GAG | GAT | GTT | TCA | TGG | ACC | GAT | TTC | TTC | 1219 |
| Arg | Met | Thr | Thr | Gln | Ser | Gln | Glu | Asp | Val | Ser | Trp | Thr | Asp | Phe | Phe |      |
|     | 355 |     |     |     |     | 360 |     |     |     |     | 365 |     |     |     |     |      |
| GAC | CCA | ATC | TCA | CAT | CCA | ATG | GGA | CAA | GGT | CAT | CAA | ACA | GAA | AGC | AAG | 1267 |
| Asp | Pro | Ile | Ser | His | Pro | Met | Gly | Gln | Gly | His | Gln | Thr | Glu | Ser | Lys |      |
| 370 |     |     |     |     | 375 |     |     |     |     | 380 |     |     |     |     | 385 |      |
| GGA | CAC | TCA | AGT | GGG | AAT | CAA | GAC | AGT | GGA | GTG | ACC | ACA | ACT | TCT | GGT | 1315 |
| Gly | His | Ser | Ser | Gly | Asn | Gln | Asp | Ser | Gly | Val | Thr | Thr | Thr | Ser | Gly |      |
|     |     |     |     | 390 |     |     |     |     | 395 |     |     |     |     | 400 |     |      |
| CCT | GCG | AGG | AGA | CCT | CAG | ATT | CCA | GAG | TGG | CTT | ATC | ATC | TTG | GCA | TCC | 1363 |
| Pro | Ala | Arg | Arg | Pro | Gln | Ile | Pro | Glu | Trp | Leu | Ile | Ile | Leu | Ala | Ser |      |
|     |     |     | 405 |     |     |     |     | 410 |     |     |     |     | 415 |     |     |      |
| CTC | CTG | GCG | CTG | GCT | CTG | ATT | CTT | GCC | GTC | TGC | ATT | GCT | GTC | AAC | AGT | 1411 |
| Leu | Leu | Ala | Leu | Ala | Leu | Ile | Leu | Ala | Val | Cys | Ile | Ala | Val | Asn | Ser |      |
|     |     | 420 |     |     |     |     | 425 |     |     |     |     | 430 |     |     |     |      |
| AGG | AGA | AGG | TGT | GGG | CAG | AAG | AAG | AAG | CTG | GTG | ATC | AAC | AGT | GGC | AAT | 1459 |
| Arg | Arg | Arg | Cys | Gly | Gln | Lys | Lys | Lys | Leu | Val | Ile | Asn | Ser | Gly | Asn |      |
|     | 435 |     |     |     |     | 440 |     |     |     |     | 445 |     |     |     |     |      |
| GGA | ACA | GTG | GAA | GAC | AGG | AAA | CCA | AGT | GAA | CTC | AAC | GGG | GAG | GCC | AGC | 1507 |
| Gly | Thr | Val | Glu | Asp | Arg | Lys | Pro | Ser | Glu | Leu | Asn | Gly | Glu | Ala | Ser |      |
| 450 |     |     |     |     | 455 |     |     |     |     | 460 |     |     |     |     | 465 |      |
| AAG | TCT | CAG | GAA | ATG | GTG | CAT | TTG | GTG | AAC | AAG | GAA | CCA | ACA | GAG | ACT | 1555 |
| Lys | Ser | Gln | Glu | Met | Val | His | Leu | Val | Asn | Lys | Glu | Pro | Thr | Glu | Thr |      |
|     |     |     |     | 470 |     |     |     |     | 475 |     |     |     |     | 480 |     |      |
| CCG | GAC | CAG | TTT | ATG | ACA | GCT | GAT | GAG | ACC | CGG | AAT | CTG | CAG | AGT | GTG | 1603 |
| Pro | Asp | Gln | Phe | Met | Thr | Ala | Asp | Glu | Thr | Arg | Asn | Leu | Gln | Ser | Val |      |
|     |     |     | 485 |     |     |     |     | 490 |     |     |     |     | 495 |     |     |      |
| GAT | ATG | AAG | ATT | GGG | GTG | TAGTGCCTAT | | GCCACTAACT | | TGAAAAGACA | | | | | | 1651 |
| Asp | Met | Lys | Ile | Gly | Val |     |     |     |     |     |     |     |     |     |     |      |
|     |     | 500 |     |     |     |     |     |     |     |     |     |     |     |     |     |      |

CAACAATTGG AGACATGTCA TTACTGGGAG CTGGGACCCT TAACAGATGC AATGTGCTAC    1711

-continued

| | | | | | |
|---|---|---|---|---|---|
| TGATTATTTT | TTATTGGGAT | TATTTTGGGC | ATAAAATTTC | CCTTTTTTTG | TTTTTTAAAA | 1771
| GTTTGTTTTC | CAATTTATGA | AAATAGCATT | GCTTCTGAA | ATGAGGGTCT | CTTCCAGTTC | 1831
| CTCCTTAGAG | GCCTTGCATT | ACCAGGGTAT | GCTACCATAG | GCTTCTACCA | AATGAATACT | 1891
| CTTGGTCCCG | ATTGAACCCA | AAGTCCCAGG | TAACATCCAC | CAGCTAAGGA | TTTCCCCAGA | 1951
| ACTTAGAGAG | ATTGGTCTCT | GGGAGGAAAT | TTGAATGGGT | CCATATTGCC | TCCCAGCAGT | 2011
| CCAATCTGTA | GGCATTGCTT | TGCAGTGGAT | GGGAGATCAG | GTGTACTGGT | TACACACTCT | 2071
| CTTTATAGAC | TCCCTTCTGC | TGGAAAATTT | CCACATGCTT | CTGAGAGATT | CCCCAAAGGT | 2131
| GACGCTATTT | ATCTTTAGTA | AGCTATTTAT | CTTTGTTTTT | GAAATATCAA | ACCCTGGAGG | 2191
| TCCTTTTTTC | AGTATGACTT | TTTTTATTTT | GTTTTTTTTT | ATTTTGTTTT | TTAGGTTACT | 2251
| TTGTCAGAAG | CATAACAGGG | TATAAGTTGA | TTCATAATAA | ATACCTGTCC | ATCTTCCATC | 2311
| TTGACCTGTT | GTGCTGTGAT | CCTTCAGTTT | CTAAATCAGC | AAGGTCTGAG | TCTTTGTAGC | 2371
| ACATCAATGT | GACCTTAGTA | TGGTCCTCTG | AAACTCATGT | TAGAGCATCC | GTGCCCTGCT | 2431
| TGGGTTTACC | CAGCTGAATC | TCAGAAGATC | AAGGACAGGA | GCACTGTTTT | CATTCTAGGA | 2491
| CTATCAAAGG | GGTTTCTCTC | CTGTTCAAGA | ATCTGAATTG | GGAGTAGGAG | AGCTTCTGTC | 2551
| CCTTTTATGT | TTCGATAACC | ACCCATTTCT | CTTTCTTAAA | GGGCACATTA | AGTTTTTATA | 2611
| TCTTACAACA | TTCGCGGTCC | TGTTTCATAG | ACACTGATCT | TATTGGCACT | TTCACAAAAC | 2671
| AGTGTGGAGG | GGACTTCTGA | CACCTTATAG | TAAAAGGAGA | AGCCAACAGA | AATGAAAGTG | 2731
| TGGACAGAGA | GCAGTAGATT | GGCATGAGGA | GGCATGATGT | ACAACCCCCA | GACCACTCTT | 2791
| TCCATCACCA | CATTTGTTGA | TGCTTTCGCA | AGCCAGTTGG | TACTTAGAAT | CAGTTCCCCA | 2851
| GGGAATCCTT | CAAAAAGCCA | TAAGAATGCC | CACCCCTGGA | ATCTTACCAC | CACCAGATGA | 2911
| GCAGGTTTAT | GGTTTAGCAA | AAGGAGAATG | CTGTCACCCT | CTGACCTCAT | AGTTTTCACA | 2971
| TACTGGGCAA | GTGTTCATCT | GCCAGGATGC | CCCATTGCTC | CTAGGTCTTC | CCAGGTACCT | 3031
| TGTAGAAGAA | CTTAAATCTA | TAAAATAAGG | CTTTCTCTAA | AATGGAACTT | CCTTTCTAAG | 3091
| GCTCCCATTT | TTACTGTTGA | CTAAATTTAT | ATGTTTAATA | GTTTTTTTC | AAATAAAAAC | 3151
| AAACACAAAA | AGGAAAAAAA | AAAAAAAAAA | AAAAAAAAA | AAAAAAAAA | AAAAA | 3207

( 2 ) INFORMATION FOR SEQ ID NO:2:

( i ) SEQUENCE CHARACTERISTICS:
        ( A ) LENGTH: 503 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Asp  Lys  Val  Trp  Trp  His  Thr  Ala  Trp  Gly  Leu  Leu  Cys  Leu  Leu
 1                  5                   10                          15

Gln  Leu  Ser  Leu  Ala  Gln  Gln  Gln  Ile  Asp  Leu  Asn  Ile  Thr  Cys  Arg
                20                   25                       30

Tyr  Ala  Gly  Val  Phe  His  Val  Glu  Lys  Asn  Gly  Arg  Tyr  Ser  Ile  Ser
               35                    40                      45

Arg  Thr  Glu  Ala  Ala  Asp  Leu  Cys  Glu  Ala  Phe  Asn  Thr  Thr  Leu  Pro
         50                    55                     60

Thr  Met  Ala  Gln  Met  Glu  Leu  Ala  Leu  Arg  Lys  Gly  Phe  Glu  Thr  Cys
 65                  70                      75                         80

Arg  Tyr  Gly  Phe  Ile  Glu  Gly  His  Val  Val  Ile  Pro  Arg  Ile  His  Pro
                85                     90                      95
```

-continued

| | | | | | | | | | | | | | | |
|---|---|---|---|---|---|---|---|---|---|---|---|---|---|---|
| Asn | Ala | Ile | Cys<br>100 | Ala | Ala | Asn | Asn | Thr<br>105 | Gly | Val | Tyr | Ile<br>110 | Leu | Leu | Ala |
| Ser | Asn | Thr<br>115 | Ser | His | Tyr | Asp<br>120 | Thr | Tyr | Cys | Phe | Asn<br>125 | Ala | Ser | Ala | Pro |
| Leu | Glu<br>130 | Glu | Asp | Cys | Thr | Ser<br>135 | Val | Thr | Asp | Leu | Pro<br>140 | Asn | Ser | Phe | Asp |
| Gly<br>145 | Pro | Val | Thr | Ile | Thr<br>150 | Ile | Val | Asn | Arg | Asp<br>155 | Gly | Thr | Arg | Tyr | Ser<br>160 |
| Lys | Lys | Gly | Glu | Tyr<br>165 | Arg | Thr | His | Gln | Glu<br>170 | Asp | Ile | Asp | Ala | Ser<br>175 | Asn |
| Ile | Ile | Asp | Glu<br>180 | Asp | Val | Ser | Ser | Gly<br>185 | Ser | Thr | Ile | Glu | Lys<br>190 | Ser | Thr |
| Pro | Glu | Gly<br>195 | Tyr | Ile | Leu | His | Thr<br>200 | Asp | Leu | Pro | Thr | Ser<br>205 | Gln | Pro | Thr |
| Gly | Asp<br>210 | Arg | Asp | Asp | Ala | Phe<br>215 | Phe | Ile | Gly | Ser | Thr<br>220 | Leu | Ala | Thr | Ile |
| Ala<br>225 | Thr | Thr | Pro | Trp | Val<br>230 | Ser | Ala | His | Thr | Lys<br>235 | Gln | Asn | Gln | Glu | Arg<br>240 |
| Thr | Gln | Trp | Asn | Pro<br>245 | Ile | His | Ser | Asn | Pro<br>250 | Glu | Val | Leu | Leu | Gln<br>255 | Thr |
| Thr | Thr | Arg | Met<br>260 | Thr | Asp | Ile | Asp | Arg<br>265 | Asn | Ser | Thr | Ser | Ala<br>270 | His | Gly |
| Glu | Asn | Trp<br>275 | Thr | Gln | Glu | Pro | Gln<br>280 | Pro | Pro | Phe | Asn | Asn<br>285 | His | Glu | Tyr |
| Gln | Asp<br>290 | Glu | Glu | Glu | Thr | Pro<br>295 | His | Ala | Thr | Ser | Thr<br>300 | Thr | Trp | Ala | Asp |
| Pro<br>305 | Asn | Ser | Thr | Thr | Glu<br>310 | Glu | Ala | Ala | Thr | Gln<br>315 | Lys | Glu | Lys | Trp | Phe<br>320 |
| Glu | Asn | Glu | Trp | Gln<br>325 | Gly | Lys | Asn | Pro | Pro<br>330 | Thr | Pro | Ser | Glu | Asp<br>335 | Ser |
| His | Val | Thr | Glu<br>340 | Gly | Thr | Thr | Ala | Ser<br>345 | Ala | His | Asn | Asn | His<br>350 | Pro | Ser |
| Gln | Arg | Met<br>355 | Thr | Thr | Gln | Ser | Gln<br>360 | Glu | Asp | Val | Ser | Trp<br>365 | Thr | Asp | Phe |
| Phe | Asp<br>370 | Pro | Ile | Ser | His | Pro<br>375 | Met | Gly | Gln | Gly | His<br>380 | Gln | Thr | Glu | Ser |
| Lys<br>385 | Gly | His | Ser | Ser | Gly<br>390 | Asn | Gln | Asp | Ser | Gly<br>395 | Val | Thr | Thr | Thr | Ser<br>400 |
| Gly | Pro | Ala | Arg | Arg<br>405 | Pro | Gln | Ile | Pro | Glu<br>410 | Trp | Leu | Ile | Ile | Leu<br>415 | Ala |
| Ser | Leu | Leu | Ala<br>420 | Leu | Ala | Leu | Ile | Leu<br>425 | Ala | Val | Cys | Ile | Ala<br>430 | Val | Asn |
| Ser | Arg | Arg<br>435 | Arg | Cys | Gly | Gln | Lys<br>440 | Lys | Lys | Leu | Val | Ile<br>445 | Asn | Ser | Gly |
| Asn | Gly<br>450 | Thr | Val | Glu | Asp | Arg<br>455 | Lys | Pro | Ser | Glu | Leu<br>460 | Asn | Gly | Glu | Ala |
| Ser<br>465 | Lys | Ser | Gln | Glu | Met<br>470 | Val | His | Leu | Val | Asn<br>475 | Lys | Glu | Pro | Thr | Glu<br>480 |
| Thr | Pro | Asp | Gln | Phe<br>485 | Met | Thr | Ala | Asp | Glu<br>490 | Thr | Arg | Asn | Leu | Gln<br>495 | Ser |
| Val | Asp | Met | Lys | Ile<br>500 | Gly | Val | | | | | | | | | |

5,506,119

( 2 ) INFORMATION FOR SEQ ID NO:3:

( i ) SEQUENCE CHARACTERISTICS:
        ( A ) LENGTH: 1062 base pairs
        ( B ) TYPE: nucleic acid
        ( C ) STRANDEDNESS: double
        ( D ) TOPOLOGY: linear ( i i ) MOLECULE TYPE: cDNA ( v i i ) IMMEDIATE SOURCE:
        ( B ) CLONE: human cDNA ( i x ) FEATURE:
        ( A ) NAME/KEY: CDS
        ( B ) LOCATION: 1..1062

( x i ) SEQUENCE DESCRIPTION: SEQ ID NO:3:

```
GTA  CAC  CCC  ATC  CCA  GAC  GAA  GAC  AGT  CCC  TGG  ATC  ACC  GAC  AGC  ACA    48
Val  His  Pro  Ile  Pro  Asp  Glu  Asp  Ser  Pro  Trp  Ile  Thr  Asp  Ser  Thr
 1              5                        10                       15

GAC  AGA  ATC  CCT  GCT  ACC  ACA  GGC  TGG  GAG  CCA  AAT  GAA  GAA  AAT  GAA    96
Asp  Arg  Ile  Pro  Ala  Thr  Thr  Gly  Trp  Glu  Pro  Asn  Glu  Glu  Asn  Glu
               20                       25                       30

GAT  GAA  AGA  GAC  AGA  CAC  CTC  AGT  TTT  TCT  GGA  TCA  GGC  ATT  GAT  GAT   144
Asp  Glu  Arg  Asp  Arg  His  Leu  Ser  Phe  Ser  Gly  Ser  Gly  Ile  Asp  Asp
                    35                       40                       45

GAT  GAA  GAT  TTT  ATC  TCC  AGC  ACC  ATT  TCA  ACC  ACA  CCA  CGG  GCC  TTT   192
Asp  Glu  Asp  Phe  Ile  Ser  Ser  Thr  Ile  Ser  Thr  Thr  Pro  Arg  Ala  Phe
     50                       55                       60

GAC  CAC  ACA  AAA  CAG  AAC  CAG  GAC  TGG  ACC  CAG  TGG  AAC  CCA  AGC  CAT   240
Asp  His  Thr  Lys  Gln  Asn  Gln  Asp  Trp  Thr  Gln  Trp  Asn  Pro  Ser  His
 65                       70                       75                       80

TCA  AAT  CCG  GAA  GTG  CTA  CTT  CAG  ACA  ACC  ACA  AGG  ATG  ACT  GAT  GTA   288
Ser  Asn  Pro  Glu  Val  Leu  Leu  Gln  Thr  Thr  Thr  Arg  Met  Thr  Asp  Val
                         85                       90                       95

GAC  AGA  AAT  GGC  ACC  ACT  GCT  TAT  GAA  GGA  AAC  TGG  AAC  CCA  GAA  GCA   336
Asp  Arg  Asn  Gly  Thr  Thr  Ala  Tyr  Glu  Gly  Asn  Trp  Asn  Pro  Glu  Ala
                    100                      105                      110

CAC  CCT  CCC  CTC  ATT  CAC  CAT  GAG  CAT  CAT  GAG  GAA  GAA  GAG  ACC  CCA   384
His  Pro  Pro  Leu  Ile  His  His  Glu  His  His  Glu  Glu  Glu  Glu  Thr  Pro
               115                      120                      125

CAT  TCT  ACA  AGC  ACA  ATC  CAG  GCA  ACT  CCT  AGT  AGT  ACA  ACG  GAA  GAA   432
His  Ser  Thr  Ser  Thr  Ile  Gln  Ala  Thr  Pro  Ser  Ser  Thr  Thr  Glu  Glu
     130                      135                      140

ACA  GCT  ACC  CAG  AAG  GAA  CAG  TGG  TTT  GGC  AAC  AGA  TGG  CAT  GAG  GGA   480
Thr  Ala  Thr  Gln  Lys  Glu  Gln  Trp  Phe  Gly  Asn  Arg  Trp  His  Glu  Gly
145                      150                      155                      160

TAT  CGC  CAA  ACA  CCC  AGA  GAA  GAC  TCC  CAT  TCG  ACA  ACA  GGG  ACA  GCT   528
Tyr  Arg  Gln  Thr  Pro  Arg  Glu  Asp  Ser  His  Ser  Thr  Thr  Gly  Thr  Ala
                    165                      170                      175

GCA  GCC  TCA  GCT  CAT  ACC  AGC  CAT  CCA  ATG  CAA  GGA  AGG  ACA  ACA  CCA   576
Ala  Ala  Ser  Ala  His  Thr  Ser  His  Pro  Met  Gln  Gly  Arg  Thr  Thr  Pro
               180                      185                      190

AGC  CCA  GAG  GAC  AGT  TCC  TGG  ACT  GAT  TTC  TTC  AAC  CCA  ATC  TCA  CAC   624
Ser  Pro  Glu  Asp  Ser  Ser  Trp  Thr  Asp  Phe  Phe  Asn  Pro  Ile  Ser  His
          195                      200                      205

CCC  ATG  GGA  CGA  GGT  CAT  CAA  GCA  GGA  AGA  AGG  ATG  GAT  ATG  GAC  TCC   672
Pro  Met  Gly  Arg  Gly  His  Gln  Ala  Gly  Arg  Arg  Met  Asp  Met  Asp  Ser
     210                      215                      220

AGT  CAT  AGT  ACA  ACG  CTT  CAG  CCT  ACT  GCA  AAT  CCA  AAC  ACA  GGT  TTG   720
Ser  His  Ser  Thr  Thr  Leu  Gln  Pro  Thr  Ala  Asn  Pro  Asn  Thr  Gly  Leu
225                      230                      235                      240

GTG  GAA  GAT  TTG  GAC  AGG  ACA  GGA  CCT  CTT  TCA  ATG  ACA  ACG  CAG  CAG   768
```

|       |       |       |       |       |       |       |       |       |       |       |       |       |       |       |       |      |
|-------|-------|-------|-------|-------|-------|-------|-------|-------|-------|-------|-------|-------|-------|-------|-------|------|
| Val   | Glu   | Asp   | Leu   | Asp   | Arg   | Thr   | Gly   | Pro   | Leu   | Ser   | Met   | Thr   | Thr   | Gln   | Gln   |      |
|       |       |       |       | 245   |       |       |       |       | 250   |       |       |       |       | 255   |       |      |
| AGT   | AAT   | TCT   | CAG   | AGC   | TTC   | TCT   | ACA   | TCA   | CAT   | GAA   | GGC   | TTG   | GAA   | GAA   | GAT   | 816  |
| Ser   | Asn   | Ser   | Gln   | Ser   | Phe   | Ser   | Thr   | Ser   | His   | Glu   | Gly   | Leu   | Glu   | Glu   | Asp   |      |
|       |       |       | 260   |       |       |       |       | 265   |       |       |       |       | 270   |       |       |      |
| AAA   | GAC   | CAT   | CCA   | ACA   | ACT   | TCT   | ACT   | CTG   | ACA   | TCA   | AGC   | AAT   | AGG   | AAT   | GAT   | 864  |
| Lys   | Asp   | His   | Pro   | Thr   | Thr   | Ser   | Thr   | Leu   | Thr   | Ser   | Ser   | Asn   | Arg   | Asn   | Asp   |      |
|       |       | 275   |       |       |       |       | 280   |       |       |       |       | 285   |       |       |       |      |
| GTC   | ACA   | GGT   | GGA   | AGA   | AGA   | GAC   | CCA   | AAT   | CAT   | TCT   | GAA   | GGC   | TCA   | ACT   | ACT   | 912  |
| Val   | Thr   | Gly   | Gly   | Arg   | Arg   | Asp   | Pro   | Asn   | His   | Ser   | Glu   | Gly   | Ser   | Thr   | Thr   |      |
|       | 290   |       |       |       |       | 295   |       |       |       |       | 300   |       |       |       |       |      |
| TTA   | CTG   | GAA   | GGT   | TAT   | ACC   | TCT   | CAT   | TAC   | CCA   | CAC   | ACG   | AAG   | GAA   | AGC   | AGG   | 960  |
| Leu   | Leu   | Glu   | Gly   | Tyr   | Thr   | Ser   | His   | Tyr   | Pro   | His   | Thr   | Lys   | Glu   | Ser   | Arg   |      |
| 305   |       |       |       |       | 310   |       |       |       |       | 315   |       |       |       |       | 320   |      |
| ACC   | TTC   | ATC   | CCA   | GTG   | ACC   | TCA   | GCT   | AAG   | ACT   | GGG   | TCC   | TTT   | GGA   | GTT   | ACT   | 1008 |
| Thr   | Phe   | Ile   | Pro   | Val   | Thr   | Ser   | Ala   | Lys   | Thr   | Gly   | Ser   | Phe   | Gly   | Val   | Thr   |      |
|       |       |       |       | 325   |       |       |       |       | 330   |       |       |       |       | 335   |       |      |
| GCA   | GTT   | ACT   | GTT   | GGA   | GAT   | TCC   | AAC   | TCT   | AAT   | GTC   | AAT   | CGT   | TCC   | TTA   | TCA   | 1056 |
| Ala   | Val   | Thr   | Val   | Gly   | Asp   | Ser   | Asn   | Ser   | Asn   | Val   | Asn   | Arg   | Ser   | Leu   | Ser   |      |
|       |       |       | 340   |       |       |       |       | 345   |       |       |       |       | 350   |       |       |      |
| GGA   | GAC   |       |       |       |       |       |       |       |       |       |       |       |       |       |       | 1062 |
| Gly   | Asp   |       |       |       |       |       |       |       |       |       |       |       |       |       |       |      |

( 2 ) INFORMATION FOR SEQ ID NO:4:

( i ) SEQUENCE CHARACTERISTICS:
        ( A ) LENGTH: 354 amino acids
        ( B ) TYPE: amino acid
        ( D ) TOPOLOGY: linear ( i i ) MOLECULE TYPE: protein ( x i ) SEQUENCE DESCRIPTION: SEQ ID NO:4:

|       |       |       |       |       |       |       |       |       |       |       |       |       |       |       |
|-------|-------|-------|-------|-------|-------|-------|-------|-------|-------|-------|-------|-------|-------|-------|
| Val   | His   | Pro   | Ile   | Pro   | Asp   | Glu   | Asp   | Ser   | Pro   | Trp   | Ile   | Thr   | Asp   | Ser   | Thr   |
| 1     |       |       |       | 5     |       |       |       |       | 10    |       |       |       |       | 15    |
| Asp   | Arg   | Ile   | Pro   | Ala   | Thr   | Thr   | Gly   | Trp   | Glu   | Pro   | Asn   | Glu   | Glu   | Asn   | Glu   |
|       |       |       | 20    |       |       |       |       | 25    |       |       |       |       | 30    |       |
| Asp   | Glu   | Arg   | Asp   | Arg   | His   | Leu   | Ser   | Phe   | Ser   | Gly   | Ser   | Gly   | Ile   | Asp   | Asp   |
|       |       | 35    |       |       |       |       | 40    |       |       |       |       | 45    |       |       |
| Asp   | Glu   | Asp   | Phe   | Ile   | Ser   | Ser   | Thr   | Ile   | Ser   | Thr   | Thr   | Pro   | Arg   | Ala   | Phe   |
|       | 50    |       |       |       |       | 55    |       |       |       |       | 60    |       |       |       |
| Asp   | His   | Thr   | Lys   | Gln   | Asn   | Gln   | Asp   | Trp   | Thr   | Gln   | Trp   | Asn   | Pro   | Ser   | His   |
| 65    |       |       |       |       | 70    |       |       |       |       | 75    |       |       |       |       | 80    |
| Ser   | Asn   | Pro   | Glu   | Val   | Leu   | Leu   | Gln   | Thr   | Thr   | Thr   | Arg   | Met   | Thr   | Asp   | Val   |
|       |       |       |       | 85    |       |       |       |       | 90    |       |       |       |       | 95    |
| Asp   | Arg   | Asn   | Gly   | Thr   | Thr   | Ala   | Tyr   | Glu   | Gly   | Asn   | Trp   | Asn   | Pro   | Glu   | Ala   |
|       |       |       | 100   |       |       |       |       | 105   |       |       |       |       | 110   |       |
| His   | Pro   | Pro   | Leu   | Ile   | His   | His   | Glu   | His   | His   | Glu   | Glu   | Glu   | Glu   | Thr   | Pro   |
|       |       | 115   |       |       |       |       | 120   |       |       |       |       | 125   |       |       |
| His   | Ser   | Thr   | Ser   | Thr   | Ile   | Gln   | Ala   | Thr   | Pro   | Ser   | Ser   | Thr   | Thr   | Glu   | Glu   |
|       | 130   |       |       |       |       | 135   |       |       |       |       | 140   |       |       |       |
| Thr   | Ala   | Thr   | Gln   | Lys   | Glu   | Gln   | Trp   | Phe   | Gly   | Asn   | Arg   | Trp   | His   | Glu   | Gly   |
| 145   |       |       |       |       | 150   |       |       |       |       | 155   |       |       |       |       | 160   |
| Tyr   | Arg   | Gln   | Thr   | Pro   | Arg   | Glu   | Asp   | Ser   | His   | Ser   | Thr   | Thr   | Gly   | Thr   | Ala   |
|       |       |       |       | 165   |       |       |       |       | 170   |       |       |       |       | 175   |       |
| Ala   | Ala   | Ser   | Ala   | His   | Thr   | Ser   | His   | Pro   | Met   | Gln   | Gly   | Arg   | Thr   | Thr   | Pro   |
|       |       |       | 180   |       |       |       |       | 185   |       |       |       |       | 190   |       |
| Ser   | Pro   | Glu   | Asp   | Ser   | Ser   | Trp   | Thr   | Asp   | Phe   | Phe   | Asn   | Pro   | Ile   | Ser   | His   |
|       |       | 195   |       |       |       |       | 200   |       |       |       |       | 205   |       |       |

```
Pro  Met  Gly  Arg  Gly  His  Gln  Ala  Gly  Arg  Arg  Met  Asp  Met  Asp  Ser
     210                 215                      220

Ser  His  Ser  Thr  Thr  Leu  Gln  Pro  Thr  Ala  Asn  Pro  Asn  Thr  Gly  Leu
225                      230                 235                           240

Val  Glu  Asp  Leu  Asp  Arg  Thr  Gly  Pro  Leu  Ser  Met  Thr  Thr  Gln  Gln
               245                      250                           255

Ser  Asn  Ser  Gln  Ser  Phe  Ser  Thr  Ser  His  Glu  Gly  Leu  Glu  Glu  Asp
               260                      265                      270

Lys  Asp  His  Pro  Thr  Thr  Ser  Thr  Leu  Thr  Ser  Ser  Asn  Arg  Asn  Asp
          275                      280                      285

Val  Thr  Gly  Gly  Arg  Arg  Asp  Pro  Asn  His  Ser  Glu  Gly  Ser  Thr  Thr
     290                 295                      300

Leu  Leu  Glu  Gly  Tyr  Thr  Ser  His  Tyr  Pro  His  Thr  Lys  Glu  Ser  Arg
305                      310                 315                           320

Thr  Phe  Ile  Pro  Val  Thr  Ser  Ala  Lys  Thr  Gly  Ser  Phe  Gly  Val  Thr
               325                      330                           335

Ala  Val  Thr  Val  Gly  Asp  Ser  Asn  Ser  Asn  Val  Asn  Arg  Ser  Leu  Ser
               340                      345                      350

Gly  Asp
```

( 2 ) INFORMATION FOR SEQ ID NO:5:

( i ) SEQUENCE CHARACTERISTICS:
        ( A ) LENGTH: 355 amino acids
        ( B ) TYPE: amino acid
        ( D ) TOPOLOGY: linear ( v i i ) IMMEDIATE SOURCE:
        ( B ) CLONE: rat protein ( x i ) SEQUENCE DESCRIPTION: SEQ ID NO:5:

```
Ser  Gln  Pro  Thr  Gly  Asp  Arg  Asp  Asp  Ala  Phe  Phe  Ile  Gly  Ser  Thr
1                   5                    10                           15

Leu  Ala  Thr  Ser  Thr  Glu  Ser  Asn  Thr  Asn  Pro  Thr  Gly  Trp  Lys  Pro
               20                      25                           30

Asn  Glu  Glu  Asn  Glu  Asp  Glu  Thr  Asp  Lys  Tyr  Pro  Asn  Phe  Ser  Gly
          35                      40                      45

Ser  Gly  Ile  Asp  Asp  Asp  Glu  Asp  Phe  Ile  Ser  Ser  Thr  Ile  Ala  Thr
     50                      55                      60

Thr  Pro  Trp  Val  Ser  Ala  His  Thr  Lys  Gln  Asn  Gln  Glu  Arg  Thr  Gln
65                       70                      75                       80

Trp  Asn  Pro  Ile  His  Ser  Asn  Pro  Glu  Val  Leu  Leu  Gln  Thr  Thr  Thr
                    85                      90                           95

Arg  Met  Thr  Asp  Ile  Asp  Arg  Asn  Ser  Thr  Ser  Ala  His  Gly  Glu  Asn
               100                      105                      110

Trp  Thr  Gln  Glu  Pro  Gln  Pro  Pro  Phe  Asn  Asn  His  Glu  Tyr  Gln  Asp
          115                      120                      125

Glu  Glu  Thr  Pro  His  Ala  Thr  Ser  Thr  Thr  Trp  Ala  Asp  Pro  Asn
     130                      135                      140

Ser  Thr  Thr  Glu  Glu  Ala  Ala  Thr  Gln  Lys  Glu  Lys  Trp  Phe  Glu  Asn
145                      150                      155                      160

Glu  Trp  Gln  Gly  Lys  Asn  Pro  Pro  Thr  Pro  Ser  Glu  Asp  Ser  His  Val
               165                      170                      175

Thr  Glu  Gly  Thr  Thr  Ala  Ser  Ala  His  Asn  Asn  His  Pro  Ser  Gln  Arg
               180                      185                      190

Met  Thr  Thr  Gln  Ser  Gln  Glu  Asp  Val  Ser  Trp  Thr  Asp  Phe  Phe  Asp
```

|     |     |     |     |     | 195 |     |     |     | 200 |     |     |     | 205 |     |     |
|-----|-----|-----|-----|-----|-----|-----|-----|-----|-----|-----|-----|-----|-----|-----|-----|
| Pro | Ile | Ser | His | Pro | Met | Gly | Gln | Gly | His | Gln | Thr | Glu | Ser | Lys | Asp |
|     | 210 |     |     |     | 215 |     |     |     | 220 |     |     |     |     |     |     |
| Thr | Gly | Ser | Ser | His | Ser | Thr | Thr | Leu | Gln | Pro | Thr | Ala | Ala | Pro | Asn |
| 225 |     |     |     |     | 230 |     |     |     | 235 |     |     |     |     |     | 240 |
| Thr | His | Leu | Val | Glu | Asp | Leu | Asn | Arg | Thr | Gly | Pro | Leu | Ser | Val | Thr |
|     |     |     |     | 245 |     |     |     |     | 250 |     |     |     |     | 255 |     |
| Thr | Pro | Gln | Ser | His | Ser | Gln | Asn | Phe | Ser | Thr | Leu | Pro | Gly | Glu | Leu |
|     |     |     |     | 260 |     |     |     |     | 265 |     |     |     | 270 |     |     |
| Glu | Glu | Gly | Glu | Asp | His | Pro | Thr | Thr | Ser | Val | Leu | Pro | Ser | Ser | Thr |
|     |     |     | 275 |     |     |     |     | 280 |     |     |     |     | 285 |     |     |
| Lys | Ser | Gly | Arg | Arg | Arg | Gly | Gly | Ser | Leu | Pro | Arg | Asp | Thr | Thr | Thr |
|     | 290 |     |     |     |     | 295 |     |     |     |     |     | 300 |     |     |     |
| Ser | Leu | Glu | Gly | Tyr | Thr | Pro | Gln | Tyr | Pro | Asp | Thr | Met | Glu | Asn | Gly |
| 305 |     |     |     |     | 310 |     |     |     |     | 315 |     |     |     |     | 320 |
| Thr | Leu | Phe | Pro | Val | Thr | Pro | Ala | Lys | Thr | Glu | Val | Phe | Gly | Glu | Thr |
|     |     |     |     | 325 |     |     |     |     | 330 |     |     |     |     | 335 |     |
| Glu | Gly | Thr | Val | Ala | Thr | Asp | Ser | Asn | Phe | Asn | Val | Asp | Gly | Ser | Leu |
|     |     |     | 340 |     |     |     |     | 345 |     |     |     |     | 350 |     |     |
| Pro | Gly | Asp |     |     |     |     |     |     |     |     |     |     |     |     |     |
|     |     | 355 |     |     |     |     |     |     |     |     |     |     |     |     |     |

( 2 ) INFORMATION FOR SEQ ID NO:6:

( i ) SEQUENCE CHARACTERISTICS:
        ( A ) LENGTH: 361 amino acids
        ( B ) TYPE: amino acid
        ( D ) TOPOLOGY: linear ( v i i ) IMMEDIATE SOURCE:
        ( B ) CLONE: hCD44

( x i ) SEQUENCE DESCRIPTION: SEQ ID NO:6:

|     |     |     |     |     |     |     |     |     |     |     |     |     |     |     |     |
|-----|-----|-----|-----|-----|-----|-----|-----|-----|-----|-----|-----|-----|-----|-----|-----|
| Met | Asp | Lys | Phe | Trp | Trp | His | Ala | Ala | Trp | Gly | Leu | Cys | Leu | Val | Pro |
| 1   |     |     |     | 5   |     |     |     |     | 10  |     |     |     |     | 15  |     |
| Leu | Ser | Leu | Ala | Gln | Ile | Asp | Leu | Asn | Ile | Thr | Cys | Arg | Phe | Ala | Gly |
|     |     |     | 20  |     |     |     |     | 25  |     |     |     |     | 30  |     |     |
| Val | Phe | His | Val | Glu | Lys | Asn | Gly | Arg | Tyr | Ser | Ile | Ser | Arg | Thr | Glu |
|     |     | 35  |     |     |     |     | 40  |     |     |     |     | 45  |     |     |     |
| Ala | Ala | Asp | Leu | Cys | Lys | Ala | Phe | Asn | Ser | Thr | Leu | Pro | Thr | Met | Ala |
|     | 50  |     |     |     |     | 55  |     |     |     |     | 60  |     |     |     |     |
| Gln | Met | Glu | Lys | Ala | Leu | Ser | Ile | Gly | Phe | Glu | Thr | Cys | Arg | Tyr | Gly |
| 65  |     |     |     |     | 70  |     |     |     |     | 75  |     |     |     |     | 80  |
| Phe | Ile | Glu | Gly | His | Val | Val | Ile | Pro | Arg | Ile | His | Pro | Asn | Ser | Ile |
|     |     |     |     | 85  |     |     |     |     | 90  |     |     |     |     | 95  |     |
| Cys | Ala | Ala | Asn | Asn | Thr | Gly | Val | Tyr | Ile | Leu | Thr | Tyr | Asn | Thr | Ser |
|     |     |     | 100 |     |     |     |     | 105 |     |     |     |     | 110 |     |     |
| Gln | Tyr | Asp | Thr | Tyr | Cys | Phe | Asn | Ala | Ser | Ala | Pro | Pro | Glu | Glu | Asp |
|     |     | 115 |     |     |     |     | 120 |     |     |     |     | 125 |     |     |     |
| Cys | Thr | Ser | Val | Thr | Asp | Leu | Pro | Asn | Ala | Phe | Asp | Gly | Pro | Ile | Thr |
|     | 130 |     |     |     |     | 135 |     |     |     |     | 140 |     |     |     |     |
| Ile | Thr | Ile | Val | Asn | Arg | Asp | Gly | Thr | Arg | Tyr | Val | Gln | Lys | Gly | Glu |
| 145 |     |     |     |     | 150 |     |     |     |     | 155 |     |     |     |     | 160 |
| Tyr | Arg | Thr | Asn | Pro | Glu | Asp | Ile | Tyr | Pro | Ser | Asn | Pro | Thr | Asp | Asp |
|     |     |     |     | 165 |     |     |     |     | 170 |     |     |     |     | 175 |     |
| Asp | Val | Ser | Ser | Gly | Ser | Ser | Ser | Glu | Arg | Ser | Ser | Thr | Ser | Gly | Gly |
|     |     |     | 180 |     |     |     |     | 185 |     |     |     |     | 190 |     |     |

| Tyr | Ile | Phe | Tyr | Thr | Phe | Ser | Thr | Val | His | Pro | Ile | Pro | Asp | Glu | Asp |
|||195|||||200||||205||||

| Ser | Pro | Trp | Ile | Thr | Asp | Ser | Thr | Asp | Arg | Ile | Pro | Ala | Thr | Arg | Asp |
||210|||||215||||220|||||

| Gln | Asp | Thr | Phe | His | Pro | Ser | Gly | Gly | Ser | His | Thr | Thr | His | Glu | Ser |
|225||||230|||||235|||||240|

| Glu | Ser | Asp | Gly | His | Ser | His | Gly | Ser | Gln | Glu | Gly | Gly | Ala | Asn | Thr |
||||245|||||250|||||255||

| Thr | Ser | Gly | Pro | Ile | Arg | Thr | Pro | Gln | Ile | Pro | Glu | Trp | Leu | Ile | Ile |
||||260|||||265||||270|||

| Leu | Ala | Ser | Leu | Leu | Ala | Leu | Ala | Leu | Ile | Leu | Ala | Val | Cys | Ile | Ala |
|||275|||||280|||||285|||

| Val | Asn | Ser | Arg | Arg | Arg | Cys | Gly | Gln | Lys | Lys | Lys | Leu | Val | Ile | Asn |
||290||||||295||||300||||

| Ser | Gly | Asn | Gly | Ala | Val | Glu | Asp | Arg | Lys | Pro | Ser | Gly | Leu | Asn | Gly |
|305|||||310||||315|||||320|

| Glu | Ala | Ser | Lys | Ser | Gln | Glu | Met | Val | His | Leu | Val | Asn | Lys | Glu | Ser |
|||||325|||||330|||||335|

| Ser | Glu | Thr | Pro | Asp | Gln | Phe | Met | Thr | Ala | Asp | Glu | Thr | Arg | Asn | Leu |
||||340|||||345||||350|||

| Gln | Asn | Val | Asp | Met | Lys | Ile | Gly | Val |
|||355||||360||

( 2 ) INFORMATION FOR SEQ ID NO:7:

( i ) SEQUENCE CHARACTERISTICS:
( A ) LENGTH: 363 amino acids
( B ) TYPE: amino acid
( D ) TOPOLOGY: linear ( v i i ) IMMEDIATE SOURCE:
( B ) CLONE: mCD44

( x i ) SEQUENCE DESCRIPTION: SEQ ID NO:7:

| Met | Asp | Lys | Phe | Trp | Trp | His | Thr | Ala | Trp | Gly | Leu | Cys | Leu | Leu | Gln |
|1||||5|||||10|||||15||

| Leu | Ser | Leu | Ala | His | Gln | Gln | Ile | Asp | Leu | Asn | Val | Thr | Cys | Arg | Tyr |
||||20|||||25||||30|||

| Ala | Gly | Val | Phe | Cys | Val | Glu | Lys | Asn | Gly | Arg | Tyr | Ser | Ile | Ser | Arg |
|||35|||||40||||45||||

| Thr | Glu | Ala | Ala | Asp | Leu | Cys | Gln | Ala | Phe | Asn | Ser | Thr | Leu | Pro | Thr |
||50||||55||||60|||||

| Met | Asp | Gln | Met | Lys | Leu | Ala | Leu | Ser | Lys | Gly | Phe | Glu | Thr | Cys | Arg |
|65||||70||||75|||||80|

| Tyr | Gly | Phe | Ile | Glu | Gly | Asn | Val | Val | Ile | Pro | Arg | Ile | His | Pro | Asn |
|||||85||||90||||95||

| Ala | Ile | Cys | Ala | Ala | Asn | His | Thr | Gly | Val | Tyr | Ile | Leu | Val | Thr | Ser |
||||100|||||105|||||110||

| Asn | Thr | Ser | His | Tyr | Asp | Thr | Tyr | Cys | Phe | Asn | Ala | Ser | Ala | Pro | Pro |
|||115|||||120|||||125|||

| Glu | Glu | Asp | Cys | Thr | Ser | Val | Thr | Asp | Leu | Pro | Asn | Ser | Phe | Asp | Gly |
||130||||||135||||140||||

| Pro | Val | Thr | Ile | Thr | Ile | Val | Asn | Arg | Asp | Gly | Thr | Arg | Tyr | Ser | Lys |
|145|||||150||||155|||||160|

| Lys | Gly | Glu | Tyr | Arg | Thr | His | Gln | Glu | Asp | Ile | Asp | Ala | Ser | Asn | Ile |
|||||165|||||170|||||175|

```
Ile  Asp  Asp  Asp  Val  Ser  Ser  Gly  Ser  Thr  Ile  Glu  Lys  Ser  Thr  Pro
               180                      185                    190

Glu  Gly  Tyr  Ile  Leu  His  Thr  Tyr  Leu  Pro  Thr  Glu  Gln  Pro  Thr  Gly
               195                      200                    205

Asp  Gln  Asp  Asp  Ser  Phe  Phe  Ile  Arg  Ser  Thr  Leu  Ala  Thr  Arg  Asp
          210                      215                    220

Arg  Asp  Ser  Ser  Lys  Asp  Ser  Arg  Gly  Ser  Ser  Arg  Thr  Val  Thr  His
225                           230                235                         240

Gly  Ser  Glu  Leu  Ala  Gly  His  Ser  Ser  Ala  Asn  Gln  Asp  Ser  Gly  Val
               245                      250                         255

Thr  Thr  Thr  Ser  Gly  Pro  Met  Arg  Arg  Pro  Gln  Ile  Pro  Glu  Trp  Leu
               260                      265                    270

Ile  Ile  Leu  Ala  Ser  Leu  Leu  Ala  Leu  Ala  Leu  Ile  Leu  Ala  Val  Cys
               275                      280                    285

Ile  Ala  Val  Asn  Ser  Arg  Arg  Arg  Cys  Gly  Gln  Lys  Lys  Lys  Leu  Val
          290                      295                 300

Ile  Asn  Gly  Gly  Asn  Gly  Thr  Val  Glu  Asp  Arg  Lys  Pro  Ser  Glu  Leu
305                           310                315                         320

Asn  Gly  Glu  Ala  Ser  Lys  Ser  Gln  Glu  Met  Val  His  Leu  Val  Asn  Lys
               325                      330                         335

Glu  Pro  Ser  Glu  Thr  Pro  Asp  Gln  Cys  Met  Thr  Ala  Asp  Glu  Thr  Arg
               340                      345                    350

Asn  Leu  Gln  Ser  Val  Asp  Met  Lys  Ile  Gly  Val
               355                 360
```

(2) INFORMATION FOR SEQ ID NO:8:

(i) SEQUENCE CHARACTERISTICS:
        (A) LENGTH: 23 amino acids
        (B) TYPE: amino acid
        (D) TOPOLOGY: linear (vii) IMMEDIATE SOURCE:
        (B) CLONE: rCD44

(xi) SEQUENCE DESCRIPTION: SEQ ID NO:8:

```
Ser  Asp  Gly  Asp  Ser  Ser  Met  Asp  Pro  Arg  Gly  Gly  Phe  Asp  Thr  Val
1                   5                      10                    15

Thr  His  Gly  Ser  Glu  Leu  Ala
               20
```

TABLE 1

Metastatic spreading out of BSp73AS cells which express variant CD44 cDNA pMeta-1***

| tumour clone | local appearance | distribution in the case of metastatic autopsy | | |
|---|---|---|---|---|
| | | *LN ing | *LN par | lung |
| BSp73ASML | 0/8 | 8/8 Ø 1.5–2.5** | 8/8 Ø 2.5–5.0 | 8/8 miliary |
| BSp73AS-pSVMeta-1-14 | 0/8 | 3/8 Ø 0.3–1.2 | 3/8 Ø 1.0–4.5 | 8/8 multiple Ø 0.3–5.0 |
| BSp73AS-pSVMeta-1-15 | 0/8 | 0/8 | 0/8 | 8/8 5–20 Ø 0.3–10.0 |
| BSp73AS | 1/8 | 0/8 | 0/8 | 0/8 |
| BSp73AS-pSVneo | 0/8 | 0/8 | 0/8 | 0/8 |

**average diameter in mm
***the Table gives the stage 60 days after injection of the given cells
*LN = lymph nodes

We claim:

1. An isolated DNA fragment encoding all or part of a surface protein of metastasizing tumor cells, wherein said DNA fragment comprises a nucleotide sequence selected from the group consisting of:

(a) ATT GCA ACT ACT CCA TGG GTT TCT GCC CAC
ACA AAA CAG AAC CAG GAA CGG ACC CAG TGG
AAC CCG ATC CAT TCA AAC CCA GAA GTA CTA CTT
CAG ACA ACC ACC AGG ATG ACT GAT ATA GAC AGA
AAC AGC ACC AGT GCT CAT GGA GAA AAC TGG ACC
CAG GAA CCA CAG CCT CCT TTC AAT AAC CAT GAG
TAT CAG GAT GAA GAG GAG ACC CCA CAT GCT ACA
AGC ACA ACC TGG GCA GAT CCT AAT AGC ACA ACA
GAA GAA GCA GCT ACC CAG AAG GAG AAG TGG
TTT GAG AAT GAA TGG CAG GGG AAG AAC CCA
CCC ACC CCA AGT GAA GAC TCC CAT GTG ACA
GAA GGG ACA ACT GCC TCA GCC CAC AAC AAC
CAT CCA AGT CAA AGA ATG ACA ACA CAG AGT
CAA GAG GAT GTT TCA TGG ACC GAT TTC TTC
GAC CCA ATC TCA CAT CCA ATG GGA CAA (bases
782–1246 of SEQ ID NO: 1) and
(b) AAC CCA AGC CAT TCA AAT CCG GAA GTG CTA
CTT CAG ACA ACC ACA AGG ATG ACT GAT GTA GAC
AGA AAT GGC ACC ACT GCT TAT GAA GGA AAC TGG
AAC CCA GAA GCA CAC CCT CCC CTC ATT CAC CAT
GAG CAT CAT GAG GAA GAA GAG ACC CCA CAT TCT
ACA AGC ACA ATC CAG GCA ACT CCT AGT AGT ACA
ACG GAA GAA ACA GCT ACC CAG AAG GAA CAG
TGG TTT GGC AAC AGA TGG CAT GAG GGA TAT CGC
CAA ACA CCC AGA GAA GAC TCC CAT TCG ACA ACA
GGG ACA GCT GCA GCC TCA GCT CAT ACC AGC CAT
CCA ATG CA (bases 229–560 of SEQ ID NO: 3).

2. A recombinant DNA molecule, comprising a vector and a DNA fragment according to claim 1.

3. A recombinant DNA molecule according to claim 2, wherein said vector is an expression vector.

4. A transformed host cell comprising a DNA fragment according to claim 1.

5. A transformed host cell comprising a recombinant DNA molecule according to claim 2.

* * * * *